(12) United States Patent
Braman et al.

(10) Patent No.: US 7,238,478 B2
(45) Date of Patent: *Jul. 3, 2007

(54) COMPOSITIONS AND METHODS FOR PROTEIN ISOLATION

(75) Inventors: Jeffrey C. Braman, Carlsbad, CA (US); Carsten-Peter Carstens, San Diego, CA (US); Natalia Novoradovskaya, San Diego, CA (US); Rajesh Bagga, San Diego, CA (US); Lee Scott Basehore, Lakeside, CA (US)

(73) Assignee: Stratagene California, La Jolla, CA (US)

( * ) Notice: Subject to any disclaimer, the term of this patent is extended or adjusted under 35 U.S.C. 154(b) by 112 days.

This patent is subject to a terminal disclaimer.

(21) Appl. No.: 10/712,137

(22) Filed: Nov. 13, 2003

(65) Prior Publication Data

US 2005/0106663 A1    May 19, 2005

(51) Int. Cl.
*C12Q 1/68* (2006.01)
*G01N 33/53* (2006.01)
*C12P 21/02* (2006.01)
*C12N 15/63* (2006.01)
*C07K 14/00* (2006.01)
*C07K 1/22* (2006.01)

(52) U.S. Cl. .................. 435/6; 435/7.1; 435/69.1; 435/252.3; 435/254.11; 435/320.1; 435/325; 530/350; 530/413

(58) Field of Classification Search ............. None
See application file for complete search history.

(56) References Cited

U.S. PATENT DOCUMENTS

| | | | | |
|---|---|---|---|---|
| 5,747,334 A | * | 5/1998 | Kay et al. | 435/320.1 |
| 5,939,288 A | * | 8/1999 | Thornburg | 435/69.8 |
| 2002/0061513 A1 | | 5/2002 | Seraphin et al. | |
| 2002/0102655 A1 | * | 8/2002 | Laible et al. | 435/69.7 |
| 2005/0032173 A1 | * | 2/2005 | Rojas et al. | 435/69.7 |
| 2005/0079201 A1 | | 4/2005 | Rathenow et al. | 424/424 |
| 2005/0118646 A1 | * | 6/2005 | Boniface et al. | 435/7.1 |

OTHER PUBLICATIONS

Zheng et al., "A new expression vector for high level protein production, one step purification and direct isotopic labeling of calmodulin-binding peptide fusion proteins," Gene, vol. 186, polypeptide. 55-60, 1997.*
Keefe et al., "One-Step Purification of Recombinant Proteins Using a Nanomolar-Affinity Streptavidin-Binding Peptide, the SBP-Tag," Prot. Exp. and Purif, vol. 23, pp. 440-446, 2001.*
Hinrichsen & Blackshear, (1993) *Regulation of Peptide-Calmodulin Complexes by Protein Kinase C in vivo.* PNAS, 90:1585-1589.
Noonan, et al., (2002) *A Calmodulin Binding Site . . .* , Arch. Biochem & Biophys., 398(1):132-140.
Puig, et al., (2001) *The Tandem Affinity Purification (TAP) Method: A General Procedure of Protein Complex Purification.* Methods 24:218-229.
Rigaut, et al., (1999) *A Generic Protein Purification Method for Protein Complex Characterization and Proteome Exploration.* Nature Biotechnology, 17:1030-1032.
Stofko-Hahn, et al., (1992) *A Single Step Purification for Recombinant Proteins.* FEBS 302(3):274-278.
Terpe, K., (2003) *Overview of tag Protein Fusions: from Molecular and Biochemical Fundamentals to Commercial Systems.* Appl. Microbiol. Biotechnol., 60:523-533.
Wilson, et al., (2001) *The Use of mRNA Display to Select High-Affinity Protein-Binding Peptides.* PNAS, 98(7):3750-3755.
PCT International Search Report, PCT/US04/37819, May 19, 2006.

* cited by examiner

*Primary Examiner*—Robert A. Wax
(74) *Attorney, Agent, or Firm*—Kathleen M. Williams; Edwards Angell Palmer & Dodge, LLP

(57) ABSTRACT

The invention provides for polynucleotides and vectors comprising at least two tag sequences. The invention also provides for polynucleotides and vectors comprising a streptavidin binding peptide sequence and a calmodulin binding peptide sequence. The invention also provides for polynucleotides and vectors wherein a gene of interest is fused in frame to at least two tag sequences, for example, a streptavidin binding peptide sequence and a calmodulin binding peptide sequence. The invention also provides for the chimeric proteins encoded by these polynucleotides. The invention also provides for methods of using the polynucleotides of the invention for detecting and/isolating protein complexes or identifying a binding partner for a protein of interest.

27 Claims, 15 Drawing Sheets

FIG. 1

| Name | No. | Sequence |
|---|---|---|
| SB1 | 3 | MDEKTHCTISMNGAVPLVPHHHPQGDPLRLIHRPQGDPLRLIHRPQGDLVALPELHAEELGEPVGDLVQGFVEQVQGVVDALVWRLPPS |
| SB2 | 2 | MDEKTHCFHPGDHLVRLVEELQALAEGLQROGGRQPHRLPRRRPHHIQLLIDRAHPQAGPLRERAHQVDGRLLLQHEPQGDRLLQQPQDHPLELVWRLPPS |
| SB3 | 4 | MTRPTASSSCVRHLLIRQGEHGHQALEDRLDKARHVRLVEGDVEVLGGLDRLARLELLDDHRPLVFDHHPQRGPLQRGDLPQVVPLVRLRHAHVLGLGLAAATIT |
| SB4 | 1 | MDEKTHWGISTWRGEPLLHHPQAGRLPLDRRARHRRILGAEPGGVDHGLRLRLELLDDHRPLVGGLRRLVPLDHPQGEALDQARQPQHLLELHHRALPPALVWRLPPS |
| SB5 | 3 | MDEKTHWVNVYHPQGDLLVRGHGHDVEALHDQGLHQLDLLVGFPPEVVRALRGEVLGGLRRLVPLDHPQGEEDLGALVDDGEVLDGLVHVGVHVEDPLVCGCHHH |
| SB6 | 1 | MDEKTHWLNNFEELLARLDGLRHBEGEDHPLVLRHHPQGDGLLDQPLGRHRALDGFVREGDRPLDQGGEHRALDGVVQALRLEGHQHRRLAQRRADRHRQLVWRLPPS |
| SB7 | 1 | MDEKTHWFGTLNSPPTHWMSAVGNGKIDCSFNMNLSLNWMLSSGHPDGALDDQLEPQGDALVGRDGVVQALRLEGHQHRRLAQRRADRHRQLVWRLPPS |
| SB8 | 1 | MDEKTHCTIELNFSFTHWKLHHBPQGDALLDDGVRPHHPLADEGGLLDQGLGHRRGVVAERLARRDPEVLEGLVERHRGLVPRLRHGGERHAEPLVWRLPPS |
| SB9 | 1 | MDEKTHCNTGLYDGAADCFNELNKDVAPLVEGRHDLVEGLLLERHPQGDPLVAHRQLVHHPLLGRGERHRRALVPQQEHQPHRLQPVVDLGRRRLVWRLPPS |
| SB10 | 1 | MDEKTHWHERAQELVGGLILLHDEPQRLLLBPRGPRPLGRLVHERGHQPQPLAGRVTERADGGLLRDGGELEPLVRBGEDHLEPLDDELDAGPRGLVWRLPHHH |
| SB11 | 1 | MDEKTHWHERVHHLADGLEQHPQGQRRPLVERHRQVPRGLVRELQHEGLPLEHPAGVHVIRLHQGDDRDVDGHGRDVRGLEREVGDGPHRLVWRLPPS |
| SB12 | 4 | MDKDPLLEELEELRERLVHHPQGGILLPLRGOVGHDAERLGAEVDLRGGLLDEPQRLQHHLEPQLGLIGELQARLQPLAGEHEGDGAGLQRVPGHQGRRLVWRLPPS |
| SB13 | 2 | MEREDPLDEQLRELRBALVDHPQSGAQALHRHDGGEHVPLRRVQHRLQPGLQHHLEPVDVLPLAEEVQQVVGGLLADGVEQPGGLLHRAQRVDHPLPDHAGQVLGRLVWRLPPS |
| SB14 | 1 | MDEKTHRTLSVSLSFNDWLGQTKACWRIJVEGLHGHPQGLVRRHEVDVLPLAEEVDVLPLAEEVQQVVGGLLADGVEQPGGLLHRAQRVDHPLFEPIVLQDHPQGGPLVCGCHHH |
| SB15 | 1 | MDEKTHWLEDLKGVLKDCLKDLMDFTYKDCRSPRVQPQPLLHHDRGEPVPLLRBAGRDLGGLGPRAPRQARPLHHGRHDLHEPIVLQDHPQGGPLVCGCHHH |
| SB16 | 1 | MDEKTHWVLQLEPQGDRLGPRHGGDDVRLVGQGESVLEGLDGRPRRRRHRLPREDEHRVRALVDQVRDLAERLVEBVDGGVEALRHLGLPQDEPRSGGCHHH |
| SB17 | 2 | MDEKTHWVGDLQEPLGPLHGGVGESVPGGLVLRHHPQRDRLVDGVGPHGRALARRPBHRVEGLHHLLQRGGERLPPDGPROLGLLGGELDRADPALVWRLPPS |
| SB18 | 1 | MDEKTHCAVNVNVGLTHWCHRVAHHQPLDPHPQGDHLRLEPLGHALVDPLVQGVERVVRPLQLDVGVQRVALVEQVAEVGEGLDHEAGQAHGALVWRLPPS |
| SB19 | 1 | MDEKTYGWRGGHVVBGLAGBIEQLRARLEEHHPQGQREPLVQEVEDVDBGLVQDLHGVVAGLLDPVERLLTDWFKKPKNVSKDCKMTPYLEMYDWSGGCHHH |
| SB20 | 1 | MNEKTHCKLNFKVNLADMLAEFHGGGQGLLGRRDGVVQRLVDGVQERVERLDRDPGLGDLRLELHHRDHRLRLGGEHLLRDHPLEPDDHLVVGGLVWRLPPS |

The "No." indicates the number of times each sequence was observed. The HPQ sequence is in bold type. Defined sequences at the termini are underlined.
The six C-terminal residues are not shown.

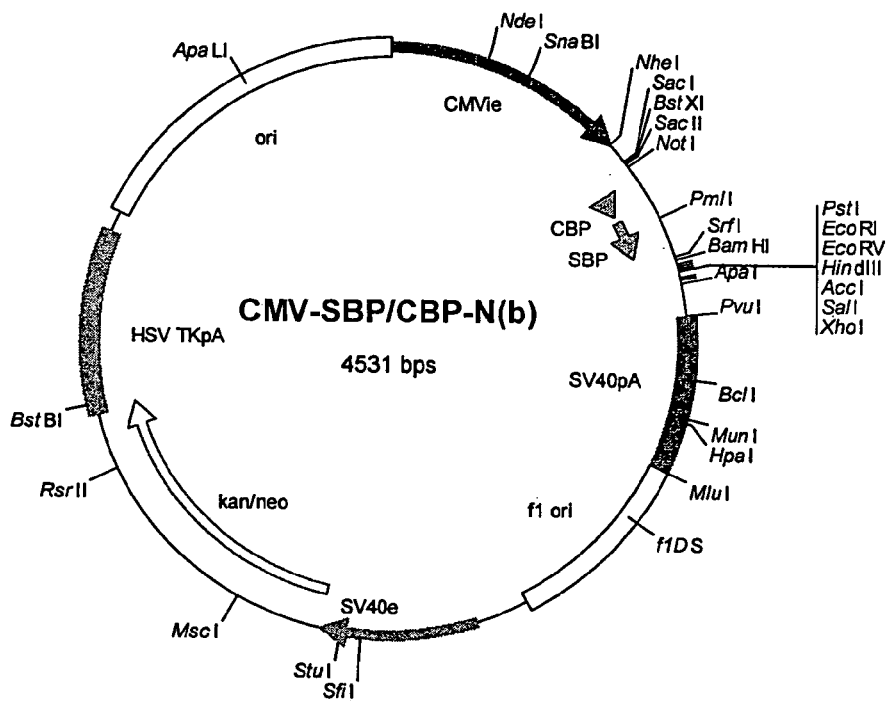

```
   1   atgcattagt  tattaatagt  aatcaattac  ggggtcatta  gttcatagcc  catatatgga
  61   gttccgcgtt  acataactta  cggtaaatgg  cccgcctggc  tgaccgccca  acgaccccg
 121   cccattgacg  tcaataatga  cgtatgttcc  catagtaacg  ccaataggga  ctttccattg
 181   acgtcaatgg  gtggagtatt  tacggtaaac  tgcccacttg  gcagtacatc  aagtgtatca
 241   tatgccaagt  acgcccccta  ttgacgtcaa  tgacggtaaa  tggcccgcct  ggcattatgc
 301   ccagtacatg  accttatggg  actttcctac  ttggcagtac  atctacgtat  tagtcatcgc
 361   tattaccatg  gtgatgcggt  tttggcagta  catcaatggg  cgtggatagc  ggtttgactc
 421   acggggattt  ccaagtctcc  accccattga  cgtcaatggg  agtttgtttt  ggcaccaaaa
 481   tcaacgggac  tttccaaaat  gtcgtaacaa  ctccgcccca  ttgacgcaaa  tgggcggtag
 541   gcgtgtacgg  tgggaggtct  atataagcag  agctggttta  gtgaaccgtc  agatccgcta
 601   gcgattacgc  caagctcgaa  attaaccctc  actaaaggga  acaaaagctg  gagctccacc
 661   gcggtggcgg  ccgccaccat  gaagcgacga  tggaaaaaga  atttcatagc  cgtctcagca
 721   gccaaccgct  taagaaaat   ctcatcctcc  ggggcacttg  gaagcggtag  cggtaccatg
 781   gacgagaaga  ccaccggctg  gcggggcggc  cacgtggtgg  agggcctggc  cggcgagctg
 841   gagcagctgc  gggccaggct  ggagcaccac  cctcagggcc  agcgggagcc  ctccggcggc
 901   tgcaagctgg  gctgcccggg  cggatccccc  gggctgcagg  aattcgatat  caagcttatc
 961   gataccgtcg  acctcgaggg  ggggcccggt  accttaatta  attaaggtac  caggtaagtg
1021   tacccaattc  gccctatagt  gagtcgtatt  acaattcact  cgatcgccct  tcccaacagt
1081   tgcgcagcct  gaatggcgaa  tggagatcca  tttttaagt   gtataatgtg  ttaaactact
1141   gattctaatt  gtttgtgtat  tttagattca  cagtcccaag  gctcatttca  ggcccctcag
1201   tcctcacagt  ctgttcatga  tcataatcag  ccataccaca  tttgtagagg  ttttacttgc
```

```
1261  tttaaaaaac ctcccacacc tccccctgaa cctgaaacat aaaatgaatg caattgttgt
1321  tgttaacttg tttattgcag cttataatgg ttacaaataa agcaatagca tcacaaattt
1381  cacaaataaa gcattttttt cactgcattc tagttgtggt ttgtccaaac tcatcaatgt
1441  atcttaacgc gtaaattgta agcgttaata ttttgttaaa attcgcgtta aattttgtt
1501  aaatcagctc atttttaac caataggccg aaatcggcaa aatcccttat aaatcaaaag
1561  aatagaccga gatagggttg agtgttgttc cagtttggaa caagagtcca ctattaaaga
1621  acgtggactc caacgtcaaa gggcgaaaaa ccgtctatca gggcgatggc ccactacgtg
1681  aaccatcacc ctaatcaagt ttttgggggt cgaggtgccg taaagcacta aatcggaacc
1741  ctaaagggag cccccgattt agagcttgac ggggaaagcc ggcgaacgtg gcgagaaagg
1801  aagggaagaa agcgaaagga gcgggcgcta gggcgctggc aagtgtagcg gtcacgctgc
1861  gcgtaaccac cacacccgcc gcgcttaatg cgccgctaca gggcgcgtca ggtggcactt
1921  ttcggggaaa tgtgcgcgga acccctattt gtttattttt ctaaatacat tcaaatatgt
1981  atccgctcat gagacaataa ccctgataaa tgcttcaata atattgaaaa aggaagaatc
2041  ctgaggcgga aagaaccagc tgtggaatgt gtgtcagtta gggtgtggaa agtccccagg
2101  ctccccagca ggcagaagta tgcaaagcat gcatctcaat tagtcagcaa ccaggtgtgg
2161  aaagtcccca ggctccccag caggcagaag tatgcaaagc atgcatctca attagtcagc
2221  aaccatagtc ccgccctaa ctccgcccat ccgcccta actccgccca gttccgccca
2281  ttctccgccc catggctgac tatttttt tatttatgca gaggccgagg ccgcctcggc
2341  ctctgagcta ttccagaagt agtgaggagg ctttttgga ggcctaggct tttgcaaaga
2401  tcgatcaaga gacaggatga ggatcgtttc gcatgattga acaagatgga ttgcacgcag
2461  gttctccggc cgcttgggtg gagaggctat tcggctatga ctgggcacaa cagacaatcg
2521  gctgctctga tgccgccgtg ttccggctgt cagcgcaggg gcgcccggtt cttttgtca
2581  agaccgacct gtccggtgcc ctgaatgaac tgcaagacga ggcagcgcgg ctatcgtggc
2641  tggccacgac gggcgttcct tgcgcagctg tgctcgacgt tgtcactgaa gcgggaaggg
2701  actggctgct attgggcgaa gtgccggggc aggatctcct gtcatctcac cttgctcctg
2761  ccgagaaagt atccatcatg gctgatgcaa tgcggcggct gcatacgctt gatccggcta
2821  cctgcccatt cgaccaccaa gcgaaacatc gcatcgagcg agcacgtact cggatggaag
2881  ccggtcttgt cgatcaggat gatctggacg aagaacatca ggggctcgcg ccagccgaac
2941  tgttcgccag gctcaaggcg agcatgcccg acggcgagga tctcgtcgtg acccatggcg
3001  atgcctgctt gccgaatatc atggtggaaa atggccgctt ttctggattc atcgactgtg
3061  gccggctggg tgtggcggac cgctatcagg acatagcgtt ggctacccgt gatattgctg
3121  aagaacttgg cggcgaatgg gctgaccgct tcctcgtgct ttacggtatc gccgctcccg
3181  attcgcagcg catcgccttc tatcgccttc ttgacgagtt cttctgagcg ggactctggg
3241  gttcgaaatg accgaccaag cgacgcccaa cctgccatca cgagatttcg attccaccgc
3301  cgccttctat gaaaggttgg gcttcggaat cgttttccgg gacgccggct ggatgatcct
3361  ccagcgcggg gatctcatgc tggagttctt cgcccaccct aggggaggc taactgaaac
3421  acggaaggag acaataccgg aaggaacccg cgctatgacg caataaaaa gacagaataa
3481  aacgcacggt gttgggtcgt ttgttcataa acgcggggtt cggtcccagg ctggcactc
3541  tgtcgatacc ccaccgagac cccattgggg ccaatacgcc cgcgtttctt cctttcccc
3601  accccacccc ccaagttcgg gtgaaggccc agggctcgca gccaacgtcg gggcggagg
3661  ccctgccata gcctcaggtt actcatatat actttagatt gatttaaaac ttcattttta
3721  atttaaaagg atctaggtga agatcctttt tgataatctc atgaccaaaa tcccttaacg
3781  tgagttttcg ttccactgag cgtcagaccc cgtagaaaag atcaaaggat cttcttgaga
3841  tcctttttt ctgcgcgtaa tctgctgctt gcaaacaaaa aaaccaccgc taccagcggt
3901  ggtttgtttg ccggatcaag agctaccaac tctttttccg aaggtaactg gcttcagcag
3961  agcgcagata ccaaatactg tccttctagt gtagccgtag ttaggccacc acttcaagaa
4021  ctctgtagca ccgcctacat acctcgctct gctaatcctg ttaccagtgg ctgctgccag
4081  tggcgataag tcgtgtctta ccgggttgga ctcaagacga tagttaccgg ataaggcgca
4141  gcggtcgggc tgaacggggg gttcgtgcac acagcccagc ttggagcgaa cgacctacac
4201  cgaactgaga tacctacagc gtgagctatg agaaagcgcc acgcttcccg aagggagaaa
4261  ggcggacagg tatccggtaa gcggcagggt cggaacagga gagcgcacga gggagcttcc
4321  agggggaaac gcctggtatc tttatagtcc tgtcgggttt cgccacctct gacttgagcg
4381  tcgatttttg tgatgctcgt caggggggcg gagcctatgg aaaaacgcca gcaacgcggc
```

Fig. 3a-2

```
4441  cttttttacgg ttcctggcct tttgctggcc ttttgctcac atgttctttc ctgcgttatc
4501  ccctgattct gtggataacc gtattaccgc c
```

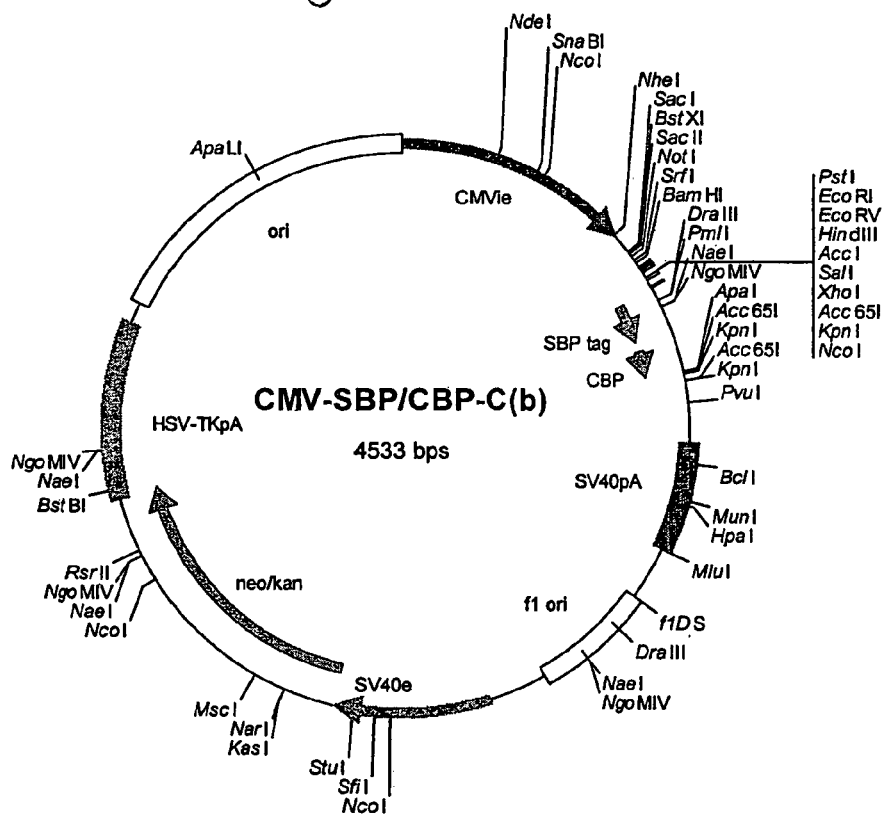

```
   1  atgcattagt tattaatagt aatcaattac ggggtcatta gttcatagcc catatatgga
  61  gttccgcgtt acataactta cggtaaatgg cccgcctggc tgaccgccca acgaccccg
 121  cccattgacg tcaataatga cgtatgttcc catagtaacg ccaataggga cttccattg
 181  acgtcaatgg gtggagtatt tacggtaaac tgcccacttg gcagtacatc aagtgtatca
 241  tatgccaagt acgccccta ttgacgtcaa tgacggtaaa tggcccgcct ggcattatgc
 301  ccagtacatg accttatggg actttcctac ttggcagtac atctacgtat tagtcatcgc
 361  tattaccatg gtgatgcggt tttggcagta catcaatggg cgtggatagc ggtttgactc
 421  acggggattt ccaagtctcc accccattga cgtcaatggg agtttgtttt ggcaccaaaa
 481  tcaacgggac tttccaaaat gtcgtaacaa ctccgcccca ttgacgcaaa tgggcggtag
 541  gcgtgtacgg tgggaggtct atataagcag agctggttta gtgaaccgtc agatccgcta
 601  gcgattacgc caagctcgaa attaaccctc actaaaggga acaaaagctg gagctccacc
 661  gcggtggcgg ccgctctagc ccgggcggat ccccgggct gcaggaattc gatatcaagc
 721  ttatcgatac cgtcgacact cgaggaagc ggtagcggta ccatggacga agaccacc
 781  ggctggcggg gcggccacgt ggtgagggc ctggccggcg agctggagca gctgcgggcc
 841  aggctggagc accacctca gggccagcgg gagccctcg gcggctgcaa gctgggctcc
 901  ggaaagcgac gatggaaaaa gaatttcata gccgtctcag cagccaaccg ctttaagaaa
 961  atctcatcct ccggggcact taggggcccg gtacttaat taattaaggt accaggtaag
1021  tgtacccaat tcgccctata gtgagtcgta ttacaattca ctcgatcgcc cttcccaaca
1081  gttgcgcagc ctgaatggcg aatggagatc caatttttaa gtgtataatg tgttaaacta
1141  ctgattctaa ttgtttgtgt atttagatt cacagtccca aggctcattt caggcccctc
```

```
1201  agtcctcaca gtctgttcat gatcataatc agccatacca catttgtaga ggttttactt
1261  gctttaaaaa acctcccaca cctccccctg aacctgaaac ataaaatgaa tgcaattgtt
1321  gttgttaact tgtttattgc agcttataat ggttacaaat aaagcaatag catcacaaat
1381  ttcacaaata aagcatttt ttcactgcat tctagttgtg gtttgtccaa actcatcaat
1441  gtatcttaac gcgtaaattg taagcgttaa tattttgtta aaattcgcgt taaattttg
1501  ttaaatcagc tcatttttta accaataggc cgaaatcggc aaaatccctt ataaatcaaa
1561  agaatagacc gagataggt tgagtgttgt tccagtttgg aacaagagtc cactattaaa
1621  gaacgtggac tccaacgtca aagggcgaaa aaccgtctat cagggcgatg cccactacg
1681  tgaaccatca ccctaatcaa gttttttggg gtcgaggtgc cgtaaagcac taaatcggaa
1741  ccctaaaggg agccccgat ttagagcttg acggggaaag ccggcgaacg tggcgagaaa
1801  ggaagggaag aaagcgaaag gagcgggcgc tagggcgctg gcaagtgtag cggtcacgct
1861  gcgcgtaacc accacaccg ccgcgcttaa tgcgccgcta cagggcgcgt caggtggcac
1921  ttttcgggga aatgtgcgcg gaacccctat ttgtttattt ttctaaatac attcaaatat
1981  gtatccgctc atgagacaat aaccctgata aatgcttcaa taatattgaa aaaggaagaa
2041  tcctgaggcg gaaagaacca gctgtggaat gtgtgtcagt tagggtgtgg aaagtcccca
2101  ggctccccag caggcagaag tatgcaaagc atgcatctca attagtcagc aaccaggtgt
2161  ggaaagtccc caggctcccc agcaggcaga agtatgcaaa gcatgcatct caattagtca
2221  gcaaccatag tcccgcccct aactccgccc atcccgcccc taactccgcc cagttccgcc
2281  cattctccgc cccatggctg actaatttt tttatttatg cagaggccga ggccgcctcg
2341  gcctctgagc tattccagaa gtagtgagga ggcttttttg gaggcctagg cttttgcaaa
2401  gatcgatcaa gagacaggat gaggatcgtt tcgcatgatt gaacaagatg gattgcacgc
2461  aggttctccg gccgcttggg tggagaggct attcggctat gactgggcac aacagacaat
2521  cggctgctct gatgccgccg tgttccggct gtcagcgcag gggcgcccgg ttcttttgt
2581  caagaccgac ctgtccggtg ccctgaatga actgcaagac gaggcagcgc ggctatcgtg
2641  gctggccacg acgggcgttc cttgcgcagc tgtgctcgac gttgtcactg aagcgggaag
2701  ggactggctg ctattgggcg aagtgccggg gcaggatctc ctgtcatctc accttgctcc
2761  tgccgagaaa gtatccatca tggctgatgc aatgcggcgg ctgcatacgc ttgatccggc
2821  tacctgccca ttcgaccacc aagcgaaaca tcgcatcgag cgagcacgta ctcggatgga
2881  agccggtctt gtcgatcagg atgatctgga cgaagaacat caggggctcg cgccagccga
2941  actgttcgcc aggctcaagg cgagcatgcc cgacggcgag gatctcgtcg tgacccatgg
3001  cgatgcctgc ttgccgaata tcatggtgga aaatggccgc ttttctggat tcatcgactg
3061  tggccggctg ggtgtggcgg accgctatca ggacatagcg ttggctaccc gtgatattgc
3121  tgaagaactt ggcggcgaat gggctgaccg cttcctcgtg ctttacggta tcgccgctcc
3181  cgattcgcag cgcatcgcct tctatcgcct tcttgacgag ttcttctgag cgggactctg
3241  gggttcgaaa tgaccgacca agcgacgccc aacctgccat cacgagattt cgattccacc
3301  gccgccttct atgaaaggtt gggcttcgga atcgttttcc gggacgccgg ctggatgatc
3361  ctccagcgcg gggatctcat gctggagttc ttcgcccacc ctaggggag gctaactgaa
3421  acacggaagg agacaatacc ggaaggaacc gcgctatga cggcaataaa aagacagaat
3481  aaaacgcacg gtgttgggtc gtttgttcat aaacgcgggg ttcggtccca gggctggcac
3541  tctgtcgata ccccaccgag acccattgg ggccaatacg cccgcgtttc ttccttttcc
3601  ccaccccacc cccaagttc gggtgaaggc ccagggctcg cagccaacgt cggggcggca
3661  ggccctgcca tagcctcagg ttactcatat atactttaga ttgatttaaa acttcatttt
3721  taatttaaaa ggatctaggt gaagatcctt tttgataatc tcatgaccaa aatcccttaa
3781  cgtgagtttt cgttccactg agcgtcagac cccgtagaaa agatcaaagg atcttcttga
3841  gatcctttt ttctgcgcgt aatctgctgc ttgcaaacaa aaaaaccacc gctaccagcg
3901  gtggtttgtt tgccggatca agagctacca actcttttc cgaaggtaac tggcttcagc
3961  agagcgcaga taccaaatac tgtccttcta gtgtagccgt agttaggcca ccacttcaag
4021  aactctgtag caccgcctac atacctcgct ctgctaatcc tgttaccagt ggctgctgcc
4081  agtggcgata agtcgtgtct taccgggttg gactcaagac gatagttacc ggataaggcg
4141  cagcggtcgg gctgaacggg gggttcgtgc acacagccca gcttggagcg aacgacctac
4201  accgaactga gatacctaca gcgtgagcta tgagaaagcg ccacgcttcc cgaagggaga
4261  aaggcggaca ggtatccggt aagcggcagg gtcggaacag gagagcgcac gagggagctt
4321  ccagggggaa acgcctggta tctttatagt cctgtcgggt ttcgccacct ctgacttgag
```

```
4381  cgtcgatttt tgtgatgctc gtcagggggg cggagcctat ggaaaaacgc cagcaacgcg
4441  gcctttttac ggttcctggc cttttgctgg cctttttgctc acatgttctt tcctgcgtta
4501  tcccctgatt ctgtggataa ccgtattacc gcc
```

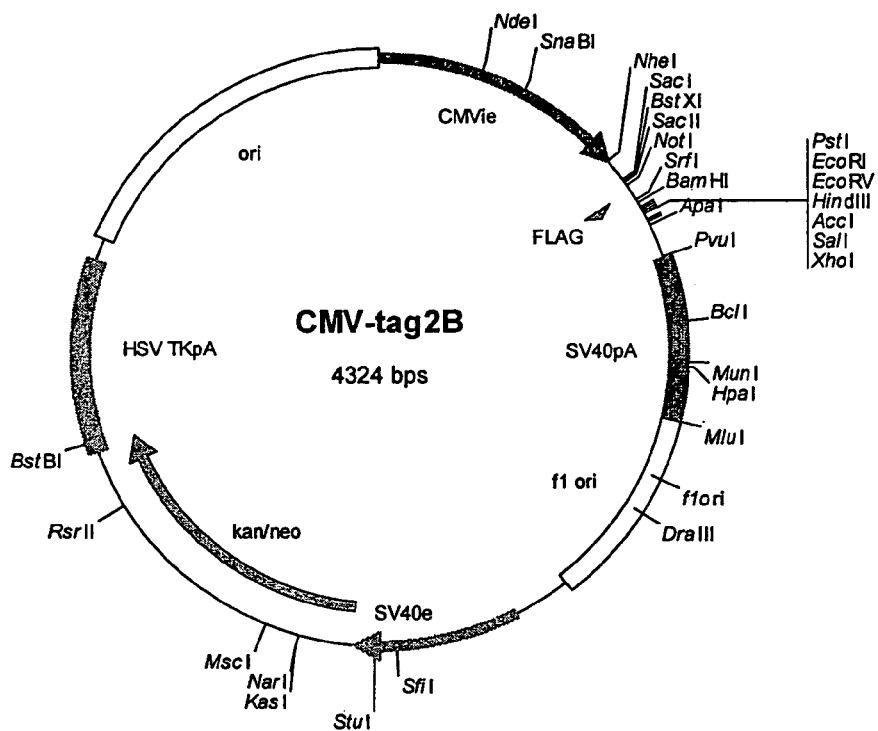

```
   1  atgcattagt tattaatagt aatcaattac ggggtcatta gttcatagcc catatatgga
  61  gttccgcgtt acataactta cggtaaatgg cccgcctggc tgaccgccca acgacccccg
 121  cccattgacg tcaataatga cgtatgttcc catagtaacg ccaataggga ctttccattg
 181  acgtcaatgg gtggagtatt tacggtaaac tgcccacttg gcagtacatc aagtgtatca
 241  tatgccaagt acgccccta ttgacgtcaa tgacggtaaa tggcccgcct ggcattatgc
 301  ccagtacatg accttatggg actttcctac ttggcagtac atctacgtat tagtcatcgc
 361  tattaccatg gtgatgcggt tttggcagta catcaatggg cgtggatagc ggtttgactc
 421  acggggattt ccaagtctcc accccattga cgtcaatggg agtttgtttt ggcaccaaaa
 481  tcaacgggac tttccaaaat gtcgtaacaa ctccgcccca ttgacgcaaa tgggcggtag
 541  gcgtgtacgg tgggaggtct atataagcag agctggttta gtgaaccgtc agatccgcta
 601  gcgattacgc caagctcgaa attaaccctc actaaaggga caaaagctg gagctccacc
 661  gcggtggcgg ccgccaccat ggattacaag gatgacgacg ataagagccc gggcggatcc
 721  cccgggctgc aggaattcga tatcaagctt atcgataccg tcgacctcga ggggggccc
 781  ggtaccttaa ttaattaagg taccaggtaa gtgtacccaa ttcgccctat agtgagtcgt
 841  attacaattc actcgatcgc ccttcccaac agttgcgcag cctgaatggc gaatggagat
 901  ccaattttta agtgtataat gtgttaaact actgattcta attgtttgtg tattttagat
 961  tcacagtccc aaggctcatt tcaggcccct cagtcctcac agtctgttca tgatcataat
1021  cagccatacc acatttgtag aggttttact tgctttaaaa acctcccac acctcccct
1081  gaacctgaaa cataaaatga atgcaattgt tgttgttaac ttgtttattg cagcttataa
1141  tggttacaaa taaagcaata gcatcacaaa tttcacaaat aaagcatttt tttcactgca
1201  ttctagttgt ggtttgtcca aactcatcaa tgtatcttaa cgcgtaaatt gtaagcgtta
```

```
1261  atatttgtt  aaaattcgcg  ttaaatttt   gttaaatcag  ctcatttttt  aaccaatagg
1321  ccgaaatcgg  caaaatccct  tataaatcaa  aagaatagac  cgagataggg  ttgagtgttg
1381  ttccagtttg  gaacaagagt  ccactattaa  agaacgtgga  ctccaacgtc  aaagggcgaa
1441  aaaccgtcta  tcagggcgat  ggcccactac  gtgaaccatc  accctaatca  agttttttgg
1501  ggtcgaggtg  ccgtaaagca  ctaaatcgga  accctaaagg  gagcccccga  tttagagctt
1561  gacggggaaa  gccggcgaac  gtggcgagaa  aggaagggaa  gaaagcgaaa  ggagcgggcg
1621  ctagggcgct  ggcaagtgta  gcggtcacgc  tgcgcgtaac  caccacaccc  gccgcgctta
1681  atgcgccgct  acagggcgcg  tcaggtggca  cttttcgggg  aaatgtgcgc  ggaacccta
1741  tttgtttatt  tttctaaata  cattcaaata  tgtatccgct  catgagacaa  taaccctgat
1801  aaatgcttca  ataatattga  aaaggaaga   atcctgaggc  ggaaagaacc  agctgtggaa
1861  tgtgtgtcag  ttagggtgtg  gaaagtcccc  aggctcccca  gcaggcagaa  gtatgcaaag
1921  catgcatctc  aattagtcag  caaccaggtg  tggaaagtcc  caggctccc   cagcaggcag
1981  aagtatgcaa  agcatgcatc  tcaattagtc  agcaaccata  gtcccgcccc  taactccgcc
2041  catcccgccc  ctaactccgc  ccagttccgc  ccattctccg  cccatggct   gactaatttt
2101  ttttatttat  gcagaggccg  aggccgcctc  ggcctctgag  ctattccaga  agtagtgagg
2161  aggcttttt   ggaggcctag  gcttttgcaa  agatcgatca  agagacagga  tgaggatcgt
2221  ttcgcatgat  tgaacaagat  ggattgcacg  caggttctcc  ggccgcttgg  gtggagaggc
2281  tattcggcta  tgactgggca  caacagacaa  tcggctgctc  tgatgccgcc  gtgttccggc
2341  tgtcagcgca  ggggcgcccg  gttcttttg   tcaagaccga  cctgtccggt  gccctgaatg
2401  aactgcaaga  cgaggcagcg  cggctatcgt  ggctggccac  gacgggcgtt  ccttgcgcag
2461  ctgtgctcga  cgttgtcact  gaagcgggaa  gggactggct  gctattgggc  gaagtgccgg
2521  ggcaggatct  cctgtcatct  caccttgctc  ctgccgagaa  agtatccatc  atggctgatg
2581  caatgcggcg  gctgcatacg  cttgatccgg  ctacctgccc  attcgaccac  caagcgaaac
2641  atcgcatcga  gcgagcacgt  actcggatgg  aagccggtct  tgtcgatcag  gatgatctgg
2701  acgaagaaca  tcagggctc   gcgccagccg  aactgttcgc  caggctcaag  gcgagcatgc
2761  ccgacggcga  ggatctcgtc  gtgacccatg  gcgatgcctg  cttgccgaat  atcatggtgg
2821  aaaatggccg  cttttctgga  ttcatcgact  gtggccggct  gggtgtggcg  gaccgctatc
2881  aggacatagc  gttggctacc  cgtgatattg  ctgaagaact  tggcggcgaa  tgggctgacc
2941  gcttcctcgt  gctttacggt  atcgccgctc  ccgattcgca  gcgcatcgcc  ttctatcgcc
3001  ttcttgacga  gttcttctga  gcgggactct  ggggttcgaa  atgaccgacc  aagcgacgcc
3061  caacctgcca  tcacgagatt  tcgattccac  cgccgccttc  tatgaaaggt  tgggcttcgg
3121  aatcgttttc  cgggacgccg  gctggatgat  cctccagcgc  ggggatctca  tgctggagtt
3181  cttcgcccac  cctaggggga  ggctaactga  aacacggaag  gagacaatac  cggaaggaac
3241  ccgcgctatg  acggcaataa  aaagacagaa  taaaacgcac  ggtgttgggt  cgtttgttca
3301  taaacgcggg  gttcggtccc  agggctggca  ctctgtcgat  accccaccga  gacccattg
3361  gggccaatac  gcccgcgttt  cttccttttc  cccacccac   ccccaagtt   cgggtgaagg
3421  cccagggctc  gcagccaacg  tcggggcggc  aggccctgcc  atagcctcag  gttactcata
3481  tatactttag  attgattaa   aacttcattt  ttaatttaaa  aggatctagg  tgaagatcct
3541  ttttgataat  ctcatgacca  aaatccctta  acgtgagttt  cgttccact   gagcgtcaga
3601  ccccgtagaa  aagatcaaag  gatcttcttg  agatcctttt  tttctgcgcg  taatctgctg
3661  cttgcaaaca  aaaaaaccac  cgctaccagc  ggtggtttgt  ttgccggatc  aagagctacc
3721  aactcttttt  ccgaaggtaa  ctggcttcag  cagagcgcag  ataccaaata  ctgtccttct
3781  agtgtagccg  tagttaggcc  accacttcaa  gaactctgta  gcaccgccta  catacctcgc
3841  tctgctaatc  ctgttaccag  tggctgctgc  cagtggcgat  aagtcgtgtc  ttaccgggtt
3901  ggactcaaga  cgatagttac  cggataaggc  gcagcggtcg  ggctgaacgg  ggggttcgtg
3961  cacacagccc  agcttggagc  gaacgaccta  caccgaactg  agatacctac  agcgtgagct
4021  atgagaaagc  gccacgcttc  ccgaagggag  aaaggcggac  aggtatccgg  taagcggcag
4081  ggtcggaaca  ggagagcgca  cgagggagct  tccaggggga  aacgcctggt  atctttatag
4141  tcctgtcggg  tttcgccacc  tctgacttga  gcgtcgattt  tgtgatgct   cgtcaggggg
4201  gcggagccta  tggaaaaacg  ccagcaacgc  ggccttttta  cggttcctgg  ccttttgctg
4261  gccttttgct  cacatgttct  ttcctgcgtt  atcccctgat  tctgtggata  accgtattac
4321  cgcc
```

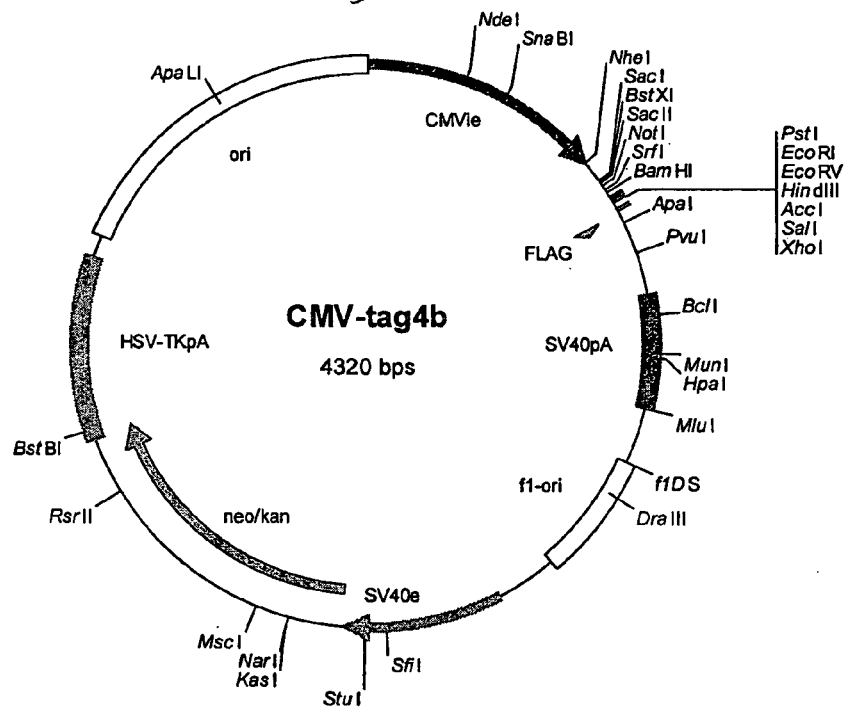

```
   1 atgcattagt tattaatagt aatcaattac ggggtcatta gttcatagcc catatatgga
  61 gttccgcgtt acataactta cggtaaatgg cccgcctggc tgaccgccca acgacccccg
 121 cccattgacg tcaataatga cgtatgttcc catagtaacg ccaatagggg ctttccattg
 181 acgtcaatgg gtggagtatt tacggtaaac tgcccacttg gcagtacatc aagtgtatca
 241 tatgccaagt acgccccta ttgacgtcaa tgacggtaaa tggcccgcct ggcattatgc
 301 ccagtacatg accttatggg actttcctac ttggcagtac atctacgtat tagtcatcgc
 361 tattaccatg gtgatgcggt tttggcagta catcaatggg cgtggatagc ggtttgactc
 421 acggggattt ccaagtctcc accccattga cgtcaatggg agtttgtttt ggcaccaaaa
 481 tcaacgggac tttccaaaat gtcgtaacaa ctccgcccca ttgacgcaaa tgggcggtag
 541 gcgtgtacgg tgggaggtct atataagcag agctggttta gtgaaccgtc agatccgcta
 601 gcgattacgc caagctcgaa attaaccctc actaaaggga acaaaagctg gagctccacc
 661 gcggtggcgg ccgctctagc ccgggcggat ccccgggct gcaggaattc gatatcaagc
 721 ttatcgatac cgtcgacact cgaggattac aaggatgacg acgataagta gggcccggta
 781 ccttaattaa ttaaggtacc aggtaagtgt acccaattcg ccctatagtg agtcgtatta
 841 caattcactc gatcgccctt cccaacagtt gcgcagcctg aatggcgaat ggagatccaa
 901 ttttttaagtg tataatgtgt taaactactg attctaattg tttgtgtatt ttagattcac
 961 agtcccaagg ctcatttcag gcccctcagt cctcacagtc tgttcatgat cataatcagc
1021 cataccacat ttgtagaggt tttacttgct ttaaaaaacc tcccacacct ccccctgaac
1081 ctgaaacata aaatgaatgc aattgttgtt gttaacttgt ttattgcagc ttataatggt
1141 tacaaataaa gcaatagcat cacaaatttc acaaataaag cattttttc actgcattct
1201 agttgtggtt tgtccaaact catcaatgta tcttaacgcg taaattgtaa gcgttaatat
1261 tttgttaaaa ttcgcgttaa attttgtta aatcagctca ttttttaacc aataggccga
1321 aatcggcaaa atcccttata aatcaaaaga atagaccgag atagggttga gtgttgttcc
1381 agtttggaac aagagtccac tattaaagaa cgtggactcc aacgtcaaag ggcgaaaaac
1441 cgtctatcag ggcgatggcc cactacgtga accatcaccc taatcaagtt ttttggggtc
1501 gaggtgccgt aaagcactaa atcggaaccc taaagggagc ccccgattta gagcttgacg
1561 gggaaagccg gcgaacgtgg cgagaaagga agggaagaaa gcgaaaggag cgggcgctag
```

```
1621  ggcgctggca agtgtagcgg tcacgctgcg cgtaaccacc acacccgccg cgcttaatgc
1681  gccgctacag ggcgcgtcag gtggcacttt tcggggaaat gtgcgcggaa cccctatttg
1741  tttattttc  taaatacatt caaatatgta tccgctcatg agacaataac cctgataaat
1801  gcttcaataa tattgaaaaa ggaagaatcc tgaggcggaa agaaccagct gtggaatgtg
1861  tgtcagttag ggtgtggaaa gtccccaggc tccccagcag gcagaagtat gcaaagcatg
1921  catctcaatt agtcagcaac caggtgtgga aagtccccag gctcccagc  aggcagaagt
1981  atgcaaagca tgcatctcaa ttagtcagca accatagtcc cgcccctaac tccgcccatc
2041  ccgcccctaa ctccgcccag ttccgcccat tctccgcccc atggctgact aattttttt
2101  atttatgcag aggccgaggc cgcctcggcc tctgagctat tccagaagta gtgaggaggc
2161  ttttttggag gcctaggctt ttgcaaagat cgatcaagag acaggatgag gatcgtttcg
2221  catgattgaa caagatggat tgcacgcagg ttctccggcc gcttgggtgg agaggctatt
2281  cggctatgac tgggcacaac agacaatcgg ctgctctgat gccgccgtgt tccggctgtc
2341  agcgcagggg cgcccggttc ttttgtcaa  gaccgacctg tccggtgccc tgaatgaact
2401  gcaagacgag gcagcgcggc tatcgtggct ggccacgacg ggcgttcctt gcgcagctgt
2461  gctcgacgtt gtcactgaag cgggaaggga ctggctgcta tgggcgaag  tgccggggca
2521  ggatctcctg tcatctcacc ttgctcctgc cgagaaagta tccatcatgg ctgatgcaat
2581  gcggcggctg catacgcttg atccggctac ctgcccattc gaccaccaag cgaaacatcg
2641  catcgagcga gcacgtactc ggatggaagc cggtcttgtc gatcaggatg atctggacga
2701  agaacatcag gggctcgcgc cagccgaact gttcgccagg ctcaaggcga gcatgcccga
2761  cggcgaggat ctcgtcgtga cccatggcga tgcctgcttg ccgaatatca tggtggaaaa
2821  tggccgcttt tctggattca tcgactgtgg ccggctgggt gtggcggacc gctatcagga
2881  catagcgttg gctacccgtg atattgctga agaacttggc ggcgaatggg ctgaccgctt
2941  cctcgtgctt tacggtatcg ccgctcccga ttcgcagcgc atcgccttct atcgccttct
3001  tgacgagttc ttctgagcgg gactctgggg ttcgaaatga ccgaccaagc gacgcccaac
3061  ctgccatcac gagatttcga ttccaccgcc gccttctatg aaaggttggg cttcggaatc
3121  gttttccggg acgccggctg gatgatcctc cagcgcgggg atctcatgct ggagttcttc
3181  gcccaccta  ggggaggct  aactgaaaca cggaaggaga caataccgga aggaacccgc
3241  gctatgacgg caataaaaag acagaataaa acgcacggtg ttgggtcgtt tgttcataaa
3301  cgcggggttc ggtcccaggg ctggcactct gtcgataccc caccgagacc ccattggggc
3361  caatacgccc gcgtttcttc cttttcccca ccccacccc  caagttcggg tgaaggccca
3421  gggctcgcag ccaacgtcgg ggcggcaggc cctgccatag cctcaggtta ctcatatata
3481  ctttagattg atttaaaact tcatttttaa tttaaaagga tctaggtgaa gatcctttt
3541  gataatctca tgaccaaaat cccttaacgt gagttttcgt tccactgagc gtcagacccc
3601  gtagaaaaga tcaaaggatc ttcttgagat ccttttttc  tgcgcgtaat ctgctgcttg
3661  caaacaaaaa aaccaccgct accagcggtg gtttgtttgc cggatcaaga gctaccaact
3721  cttttccga  aggtaactgg cttcagcaga gcgcagatac caaatactgt ccttctagtg
3781  tagccgtagt taggccacca cttcaagaac tctgtagcac cgcctacata cctcgctctg
3841  ctaatcctgt taccagtggc tgctgccagt ggcgataagt cgtgtcttac cgggttggac
3901  tcaagacgat agttaccgga taaggcgcag cggtcgggct gaacggggg  ttcgtgcaca
3961  cagcccagct tggagcgaac gacctacacc gaactgagat acctacagcg tgagctatga
4021  gaaagcgcca cgcttcccga agggagaaag gcggacaggt atccggtaag cggcagggtc
4081  ggaacaggag agcgcacgag ggagcttcca ggggaaacg  cctggtatct ttatagtcct
4141  gtcgggtttc gccacctctg acttgagcgt cgatttttgt gatgctcgtc agggggcgg
4201  agcctatgga aaaacgccag caacgcggcc ttttacggt  tcctggcctt ttgctggcct
4261  tttgctcaca tgttctttcc tgcgttatcc cctgattctg tggataaccg tattaccgcc
```

Fig. 4b-2 ately, the invention provides for a
COMPOSITIONS AND METHODS FOR PROTEIN ISOLATION

FIELD OF THE INVENTION

The invention relates in general to improved methods of protein isolation and identification of protein binding partners for a protein of interest.

BACKGROUND OF THE INVENTION

Identification of protein/protein interactions is at the core of understanding the biological processes occurring in living cells. Traditionally, the potential interacting proteins have been identified by genetic methods (two hybrid screens) with subsequent verification of the interaction by co-immunoprecipitation. While this method has been very successful for detection of two interacting proteins, it is of limited utility when more complex protein aggregates such as ribosomes, splice complexes or transcription complexes are investigated.

To identify and isolate yeast complex protein aggregates, an alternative method has been developed by Seraphin et al. (Rigaut et al., 1999, *Nature Biotech.*, 17:1030-1032; Puig et al., 2001, *Methods*, 24: 218-219; U.S. 2002/0061513, reviewed in Terpe et al., 2003, *App. Microbiol. Biotechnol.*, 60:523-533). This method combines purification of the protein complex of interest using two different affinity purification tags fused to at least one known protein component of a complex of interest by genetic methods, with subsequent mass spectroscopy to identify the unknown components of the isolated complex. The use of two consecutive purification steps allows for isolation of the complex, in a purified form, without disruption of the targeted complex. Only certain combinations of purification tags are suitable for this method.

The calmodulin-binding domain of the calmodulin binding peptide (CBP-tag) and the IgG binding domain(s) of *Staphylococcus aureus* protein A represent an efficient combination of purification tags, according to this method (Rigaut et al., supra; Puig et al., supra; U.S. 2002/0061513). The interaction between the CBP-tag and the purification matrix (immobilized calmodulin) can be controlled by the presence of $Ca^{2+}$. In the presence of $Ca^{2+}$, the CBP tag binds to the purification matrix whereas removal of $Ca^{2+}$ with a chelating agent such as EGTA, allows recovery of the tagged protein from the purification resin under mild conditions (Stofko-Hahn et al., 1992, *FEBS Lett.*, 302:274-278). The IgG-binding domain of protein A provides specific, high affinity binding with little non-specific interaction. However, it is very difficult to elute protein A tagged proteins from IgG-columns. Consequently, elution can only be achieved by removing protein A fusion proteins by digestion with a site-specific protease. Utilization of the IgG-binding domain of protein A therefore requires additional processing steps and leads to contamination of the purified protein with the protease.

There is a need in the art for a method to detect and identify protein complexes that does not disrupt protein-protein interactions. This method will also facilitate detection of binding partners for a protein of interest in the absence of prior knowledge of the binding partner(s) or the function of the protein complex. There is also a need in the art for a purification protocol for protein complexes that does not require digestion with a protease enzyme. This method provides a simple, generic purification protocol that can be used routinely, and, possibly, in an automated system, for the purification of protein complexes and for proteome analysis.

SUMMARY OF THE INVENTION

The invention provides reagents for detecting and isolating proteins in a complex. In particular, the invention provides for a vector comprising at least two affinity tags. The invention provides for a protein comprising at least two affinity tags. Alternatively, the invention provides for a protein of interest comprising at least one affinity tag, and a binding partner, or candidate binding partner for the protein of interest comprising at least a second affinity tag. The invention also provides methods for identifying and detecting a protein in a complex, without disruption of the complex. The method of the invention can be used to find one or more "target" binding partners for a "bait" protein of interest. According to the method of the invention, the protein of interest is fused in frame, either N-terminally, C-terminally or a combination thereof, to at least two affinity tags.

In one embodiment, the invention provides for a polynucleotide comprising at least two affinity tag sequences. In one embodiment, one of the tag sequences encodes streptavidin-binding peptide having a nucleotide sequence presented in FIG. 1. The at least two tag sequences are either directly adjacent to each other or are separated by a spacer, for example, of 1-60 nucleotides. Either of the first or second tags can be located 5' of the other tag.

In one embodiment the invention provides for a polynucleotide comprising a gene of interest and at least two tag sequences. The gene of interest is fused in frame with each of the tag sequences. In one embodiment, one of the tag sequences encodes streptavidin-binding peptide having a nucleotide sequence presented in FIG. 1.

As used herein, the terms "nucleic acid", "polynucleotide" and "oligonucleotide" refer to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

As used herein, "protein of interest" means any protein for which the nucleic acid sequence is known or available, or that becomes available, such that it can be cloned into a nucleic acid vector which is suitable for expression in the appropriate host cells or cell-free expression systems. For purification of a protein complex, the nucleic acid sequence of at least one of the subunits of the protein complex must be known or available.

The invention also provides for identification and/or purification of a protein complex, or identification and/or purification of a complex of one or more proteins and one or more biomolecules. As used herein, a "biomolecule" includes a protein, peptide, nucleic acid, antibody, or other biomolecule. A biomolecule complex is a complex of at least two biomolecules, preferably at least one protein in association with either other proteins or with other biomolecules, for example, nucleic acid or antibody. The biomolecule complexes can be naturally occurring, such as nuclear snRNPs or antigen-antibody complexes, or they can be non-naturally occurring, for example, mutant DNA binding protein in association with mutant target DNA. Any complex molecule comprising as one or more subunits a polypeptide or subunit expressed according to the invention and/or further comprising other components which associate in a manner stable enough to remain associated during the affinity purification steps is a biomolecule complex that can be detected/purified by the method of the invention.

The terms "tag" or "affinity tag" are used interchangeably herein. As used herein, "tag" or "affinity tag" means a moiety that is fused in frame to the 5' or 3' end of, or internally to, the protein product of a gene of interest, a biomolecule of the invention, or another tag. A "tag" specifically binds to a ligand as a result of attractive forces that exist between the tag and a ligand. "Specifically binds" as it refers to a "tag" and a ligand means via covalent or hydrogen bonding or electrostatic attraction or via an interaction between for example a tag and a ligand, an antibody and an antigen, protein subunits, or a nucleic acid binding protein and a nucleic acid binding site. Preferably, a "tag" of the invention, binds a ligand with a dissociation constant ($K_D$) of at least about $1 \times 10^3$ M$^{-1}$, usually at least $1 \times 10^4$ M$^{-1}$, typically at least $1 \times 10^5$ M$^{-1}$, preferably at least $1 \times 10^6$ M$^{-1}$ to $1 \times 10^9$ M$^{-1}$ or more, for example $1 \times 10^{14}$ M$^{-1}$ for streptavidin-avidin binding, $1 \times 10^{15}$ M$^{-1}$, $1 \times 10^{16}$ M$^{-1}$, $1 \times 10^{20}$ M$^{-1}$, or more. A tag does not interfere with expression, folding or processing of the tagged protein or with the ability of a protein to bind to its binding partner. Tags include but are not limited to calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, maltose-binding protein, TrxA, DsbA, hemagglutinin epitope, InaD, NorpA, and GFP (see Honey et al., supra; Hu et al., supra; Puig et al., supra; Rigaut et al., supra; Terpe, supra; U.S. 2002/0061513, Kimple et al., Biotechniques. 2002, 33:578) incorporated by reference herein in their entirety.

As used herein, "fused in frame" means fused such that the correct translational reading frame is maintained thereby allowing for expression of all of the components of the chimeric or fusion protein.

As used herein, the term "fused to the amino-terminal end" refers to the linkage of a polypeptide sequence to the amino terminus of another polypeptide. The linkage may be direct or may be mediated by a short (e.g., about 2-20 amino acids) linker peptide. Examples of useful linker peptides include, but are not limited to, glycine polymers $((G)_n)$ including glycine-serine and glycine-alanine polymers. It should be understood that the amino-terminal end as used herein refers to the existing amino-terminal amino acid of a polypeptide, whether or not that amino acid is the amino terminal amino acid of the wild type or a variant form (e.g., an amino-terminal truncated form) of a given polypeptide.

As used herein, the term "fused to the carboxy-terminal end" refers to the linkage of a polypeptide sequence to the carboxyl terminus of another polypeptide. The linkage may be direct or may be mediated by a linker peptide. As with fusion to the amino-terminal end, fusion to the carboxy-terminal end refers to linkage to the existing carboxy-terminal amino acid of a polypeptide.

As used herein, steptavidin binding peptide (SBP)" or steptavidin binding protein means a synthetic streptavidin-binding domain that binds streptavidin with a dissociation constant from $1 \times 10^5$ M$^{-1}$–$5 \times 10^{10}$ M$^{-1}$ (for example, $1 \times 10^5$ M$^{-1}$, $1 \times 10^6$ M$^{-1}$, $1 \times 10^7$ M$^{-1}$, $1 \times 10^8$ M$^{-1}$, $1 \times 10^9$ M$^{-1}$, $1 \times 10^1$ M$^{-1}$ in the absence but not in the presence of biotin. In one embodiment, SBP has the amino acid sequence presented in FIG. 1. Additional SBP sequences useful according to the invention include SB1, SB2, SB5, SB9, SB11 and SB12 (Wilson et al., 2001, Proc. Natl. Acad. Sci USA, 98:3750), presented in FIG. 2.

The invention also provides for an isolated polynucleotide comprising at least two tag sequences, wherein one of the tag sequences encodes streptavidin binding peptide and the other encodes calmodulin binding peptide. The at least two tag sequences are either directly adjacent to each other or are separated by a spacer, for example, of 1-60 nucleotides. Either of the streptavidin binding peptide tag or the calmodulin binding peptide tag can be located 5' of the other tag.

The invention also provides for an isolated polynucleotide comprising a gene sequence of interest and at least two tag sequences fused in frame with each other. One of the two tag sequences encodes streptavidin binding peptide and one of the tag sequences encodes calmodulin binding peptide.

As used herein, "calmodulin binding peptide (CBP)" or calmodulin binding peptide means a peptide that binds calmodulin, preferably with a dissociation constant from $1 \times 10^3$ M$^{-1}$ to $1 \times 10^{14}$ M$^{-1}$ and preferably $1 \times 10^6$ M$^{-1}$ to $1 \times 10^{10}$ M$^{-1}$ and more preferably, $1 \times 10^7$ M$^{-1}$ to $1 \times 10^9$ M$^{-1}$, in a Ca2+ dependent manner. Binding occurs in the presence of $Ca^{2+}$, in the range of 0.1 μM to 10 mM. CBP is derived from the C-terminus of skeletal-muscle myosin light chain kinase. In the presence of $Ca^{2+}$, the CBP tag binds to calmodulin and, upon removal of $Ca^{2+}$, for example, in the presence of a chelating agent such as EGTA (preferably in the range of 0.1 μM to 10 mM), CBP does not bind calmodulin. In one embodiment, CBP has the amino acid sequence presented in FIG. 1. Additional CBP sequences useful according to the invention include: bovine neuromodulin AA 37-53 KIQAS-FRGHITRKKLKG (SEQ ID NO: 1) (Hinfichsen et al., 1993, Proc. Natl. Acad Sci USA, 90:1585); calmodulin-dependent protein kinase I (CMKI) AA 294-318 SEQIKKN-FAKSKWKQAFNATAVVRHMRK (SEQ ID NO: 2); calmodulin-dependent protein kinase II (CMKII) AA 290-309 LKKFNARRKLKGAILTTMLA (SEQ ID NO: 3); and tuberous sclerosis 2 (TSC) WIARLRHIKRLRQRIC (SEQ ID NO: 4) (Noonan et al., 2002, Arch, Biochem. Biophys. 389:32).

In one embodiment, each of the tags of the isolated polynucleotide are adjacent to the 5'end of the target gene sequence.

In another embodiment, each of the tags of the isolated polynucleotide are adjacent to the 3' end of the target gene sequence.

Since mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose rings, and as the "3' end" if its 3' oxygen is not linked to a 5' phosphate of a subsequent mononucleotide pentose ring.

As used herein, "adjacent" or "tandem" means immediately preceding or following. "Adjacent" also means preceding or following and separated by a linker, for example a nucleic acid linker of 6-60 nucleic acids or an amino acid linker of 2-20 amino acids.

The invention also provides for a vector comprising the isolated polynucleotides of the invention.

As used herein, "vector" means a cloning vector that contains the necessary regulatory sequences to allow transcription and translation of a cloned gene or genes.

The invention also provides for a cell comprising the vector of the invention.

The invention also provides for a composition comprising the isolated polynucleotides of the invention.

The invention also provides for a chimeric protein comprising at least two affinity tags, wherein one of the tags is streptavidin binding peptide having the sequence presented in FIG. 1. The at least two tags are either directly adjacent to each other or are separated by a spacer, as defined herein. Either of the first or second tags can be located N-terminal to the other tag.

The invention also provides for a chimeric protein comprising a protein of interest fused in frame to at least two different affinity tags, one of which is streptavidin binding peptide having the sequence presented in FIG. 1.

The invention also provides for a chimeric protein comprising a streptavidin binding peptide and a calmodulin binding peptide. The tags are either directly adjacent to each other or are separated by a spacer, as defined herein. Either of the first or second tags can be located N-terminal to the other tag.

The invention also provides for a chimeric protein comprising a protein of interest fused in frame to at least two different affinity tags, one of which is streptavidin binding peptide, and wherein one of the affinity tags is calmodulin binding peptide.

In one embodiment, each of the tags are adjacent to the N-terminus of the protein of interest.

In another embodiment, each of the tags are adjacent to the C-terminus of the protein of interest.

As used herein, a "chimera" or "fusion" means a fusion of a first amino acid sequence (protein) comprising a protein product of a gene of interest, joined to a second amino acid sequence encoding a first tag, and joined to at least a third amino acid sequence encoding a second tag. A "chimera" according to the invention contains three or more amino acid sequences (for example a sequence encoding a protein of interest, a sequence encoding calmodulin-binding peptide and a sequence encoding streptavidin-binding peptide) from unrelated proteins, joined to form a new functional protein. A chimera of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses chimeras wherein at least two tag amino acid sequences are joined N-terminally or C-terminally to the protein product of the gene of interest, or wherein a first tag sequence is joined N-terminally and a second tag sequence is joined C-terminally to a protein product of a gene of interest. A "chimera" of the invention includes a protein of interest fused to at least two tags, wherein the tags are located N- or C-terminally, or any combination thereof. The invention also encompasses a chimera wherein one or more of the tag amino acid sequences are fused internally to the amino acid sequence of a protein of interest.

A "chimera" according to the invention also refers to a fusion of a first amino acid sequence comprising a protein product of a gene of interest, joined to at least a second amino acid sequence encoding at least one tag of the invention.

As used herein, "chimeric or fusion protein or polypeptide" refers to a heterologous amino acid sequence of two or more "tag" amino acid sequences fused in frame to the amino acid sequence of interest. In one embodiment, the two or more tag amino acid sequences are fused to the N or C termini of the amino acid sequence of the protein of interest. In one embodiment, a first tag amino acid sequence is fused in frame to the N-terminus of the amino acid sequence of the protein of interest and the second tag amino acid sequence is fused in frame to the C-terminus of the protein of interest. The invention also provides for a first chimeric protein comprising a first tag amino acid sequence fused to a first protein of a complex and a second chimeric protein comprising a second tag amino acid sequence fused to a second protein, wherein the first and second protein are present in the same complex.

The invention also provides for a composition comprising the isolated chimeric proteins of the invention.

The invention also provides for a method of detecting or isolating one or more binding partners for a protein encoded by a gene of interest, comprising the following steps. A gene sequence of interest is cloned into a vector such that the gene of interest is fused in frame with at least two different tag sequences. One of the tag sequences encodes streptavidin binding peptide having the amino acid sequence presented in FIG. 1. The vector is introduced into a cell comprising at least one candidate binding partner. The protein product of the gene of interest and the candidate binding partner are allowed to form a complex in the cell. The complex is isolated by lysing the cells and performing at least one round of affinity purification. The protein complex is then detected.

The invention also provides for a method of detecting or isolating one or more binding partners for a protein encoded by a gene of interest, comprising the following steps. A gene sequence of interest is cloned into a vector such that the gene of interest is fused in frame with at least two different tag sequences. One of the tag sequences encodes streptavidin binding peptide and one of the tag sequences encodes calmodulin-binding peptide. The vector is introduced into a cell comprising at least one candidate binding partner. The protein product of the gene of interest and the candidate binding partner are allowed to form a complex in the cell. The complex is isolated by lysing the cells and performing at least one round of affinity purification. The protein complex is then detected.

In one embodiment, the cell comprises a vector that expresses at least one candidate binding partner for the protein product of the gene of interest.

In one embodiment the candidate binding partner expresses a tag.

The invention also provides for a method of detecting or isolating a protein complex comprising the following steps. A gene sequence of interest is cloned into a vector such that the gene sequence of interest is fused in frame with at least two different tag sequences. One of the two tag sequences encodes streptavidin binding peptide having the amino acid sequence presented in FIG. 1. The vector is introduced into a cell that expresses at least one protein binding partner for the protein product of the gene sequence of interest. The protein product of the gene of interest and the protein binding partner are allowed to form a complex. The complex is isolated by lysing the cells and performing at least one round of affinity purification.

The invention also provides for a method of detecting or isolating a protein complex comprising the following steps. A gene sequence of interest is cloned into a vector such that the gene sequence of interest is fused in frame with at least two different tag sequences. One of the two tag sequences encodes streptavidin binding peptide and one of the two tag sequences encodes calmodulin binding peptide. The vector is introduced into a cell that expresses at least one protein binding partner for the protein product of the gene sequence of interest. The protein product of the gene of interest and the protein binding partner are allowed to form a complex. The complex is isolated by lysing the cells and performing at least one round of affinity purification.

In one embodiment, the cell comprises a vector that expresses at least one candidate binding partner for the protein product of the gene of interest.

In one embodiment, the candidate binding partner comprises a tag.

In another embodiment, the complex is isolating by performing at least two successive rounds of affinity purification.

As used herein, "protein complex" means two or more proteins or biomolecules that are associated. As used herein, "associated" as it refers to binding of two or more proteins or biomolecules, means specifically bound by hydrogen bonding, covalent bonding, or via an interaction between, for example a protein and a ligand, an antibody and an antigen, protein subunits, or nucleic acid and protein. Under conditions of stable association, binding results in the formation of a protein complex, under suitable conditions, with a dissociation constant, ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$ or more, for example $1 \times 10^{14}$ $M^{-1}$, $1 \times 10^{16}$, $M^{-1}$, $1 \times 10^{18}$ $M^{-1}$, $1 \times 10^{20}$ $M^{-1m}$, $1 \times 10^{30}$ $M^{-1}$ or more, for each member of the complex. Methods of performing binding reactions between members of a protein complex, as defined herein, are well-known in the art and are described hereinbelow.

As used herein, "form a complex" means to incubate members of a protein complex under conditions, for example, in the presence of the appropriate buffer, salt conditions, and pH, that allow for association of the members of the protein complex. "Form a complex" also means to bind, under suitable conditions, with a dissociation constant ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$, for example $1 \times 10^{14}$ $M^{-1}$, $1 \times 10^{16}$, $M^{-1}$, $1 \times 10^{18}$ $M^{-1,}$ $1 \times 10^{20}$ $M^{-1m}$, $1 \times 10^{30}$ $M^{-1}$ or more, or more, for each member of the complex.

As used herein, "affinity purification" means purification of a complex via binding of at least one of the affinity tags of a member of the complex to the ligand for the affinity tag. In one embodiment, the tag is associated with a support material. In a preferred embodiment, the method of the invention utilizes at least two affinity purification steps.

As used herein, "purification resin" or "affinity purification resin" refers to a support material to which a ligand of the invention is immobilized. A "purification resin" according to the invention includes but is not limited to beaded derivatives of agarose, cellulose, polystyrene gels, cross-linked dextrans, polyacrylamide gels, and porous silica.

Further features and advantages of the invention are as follows.

BRIEF DESCRIPTION OF THE DRAWINGS

FIG. 1 shows the sequence of the CBP/SBP tandem affinity tags. FIG. 1A shows DNA (SEQ ID NO: 5) encoding peptide sequence (SEQ ID NO: 6) comprising TAP tags fused to the N-terminus of the bait protein. FIG. 1B shows DNA (SEQ ID NO: 7) encoding peptide sequence (SEQ ID NO: 8) comprising TAP tags fused to the C-terminus of the bait protein.

FIG. 2 is a Table presenting SBP sequences useful according to the invention.
SB1 is SEQ ID NO: 9; SB2is SEQ ID NO: 10; SB3 is SEQ ID NO: 11;
SB4 is SEQ ID NO: 12; SB5 is SEQ ID NO: 13; SB6 is SEQ ID NO: 14;
SB7 is SEQ ID NO: 15; SB8 is SEQ ID NO: 16; SB9 is SEQ ID NO: 17;
SB10 is SEQ ID NO: 18; SB11 is SEQ ID NO: 19; SB12 is SEQ ID NO: 20;
SB13 is SEQ ID NO: 21; SB14 is SEQ ID NO: 22; SB15 is SEQ ID NO: 23;
SB16 is SEQ ID NO: 24; SB17 is SEQ ID NO: 25; SB18 is SEQ ID NO: 26;
SB19 is SEQ ID NO: 27; SB20 is SEQ ID NO: 28.

FIG. 3(a) and 3(b) show expression vectors comprising nucleic acids encoding CBP and SBP affinity tags useful according to the invention. The nucleic acid sequence shown in FIG. 3(a) is (SEQ ID NO: 29). The nucleic acid sequence shown in FIG. 3(b) is (SEQ ID NO: 30).

FIG. 4(a) and 4(b) show expression vectors for expression of a "target" binding partner of the invention. The nucleic acid sequence shown in FIG. 4(a) is (SEQ ID NO: 31). The nucleic acid sequence shown in FIG. 4(b) is (SEQ ID NO: 32).

DESCRIPTION

Figure 5:
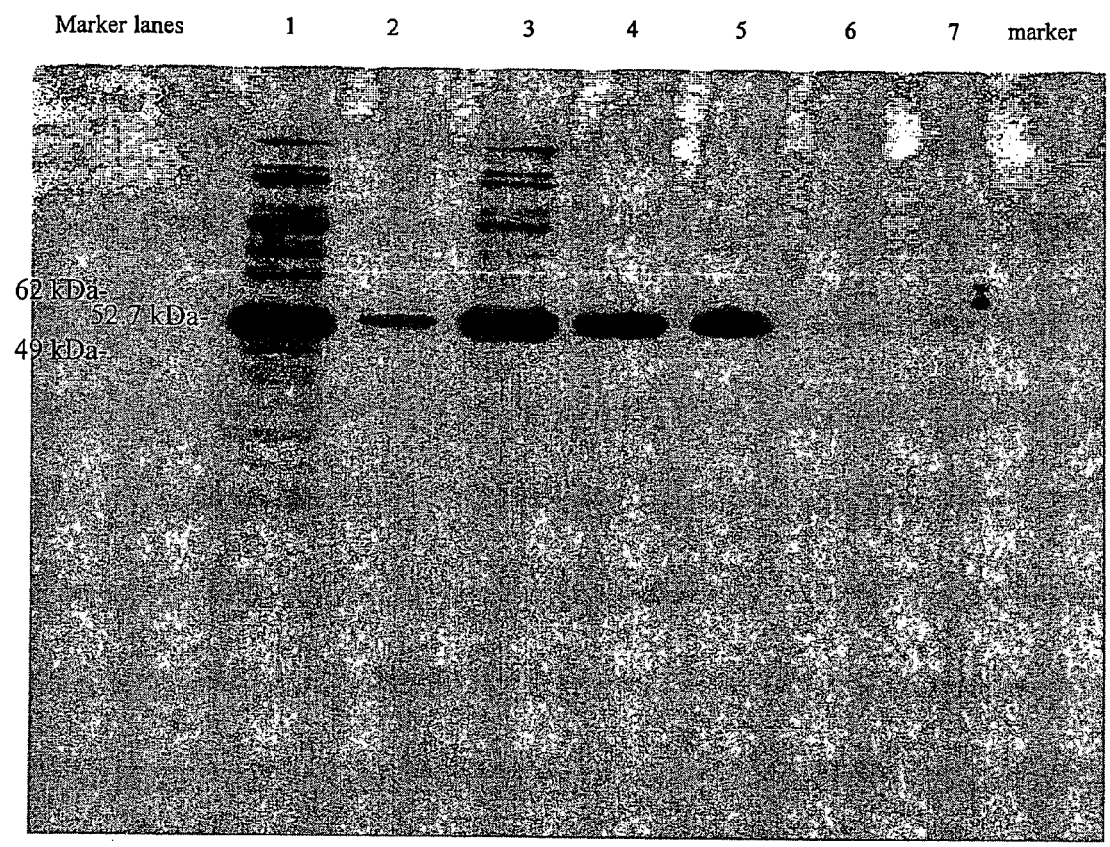
FIG. 5 is a Western blot of affinity purified Mef2c-FLAG.

The invention provides for a method of detecting and/or purifying a protein complex under mild conditions such that the complex is not dissociated. The purification methods described herein allow for isolation of a protein complex that maintains functional activity. The invention also provides for detection of binding partners for a protein of interest.

Tags

Figure 1:
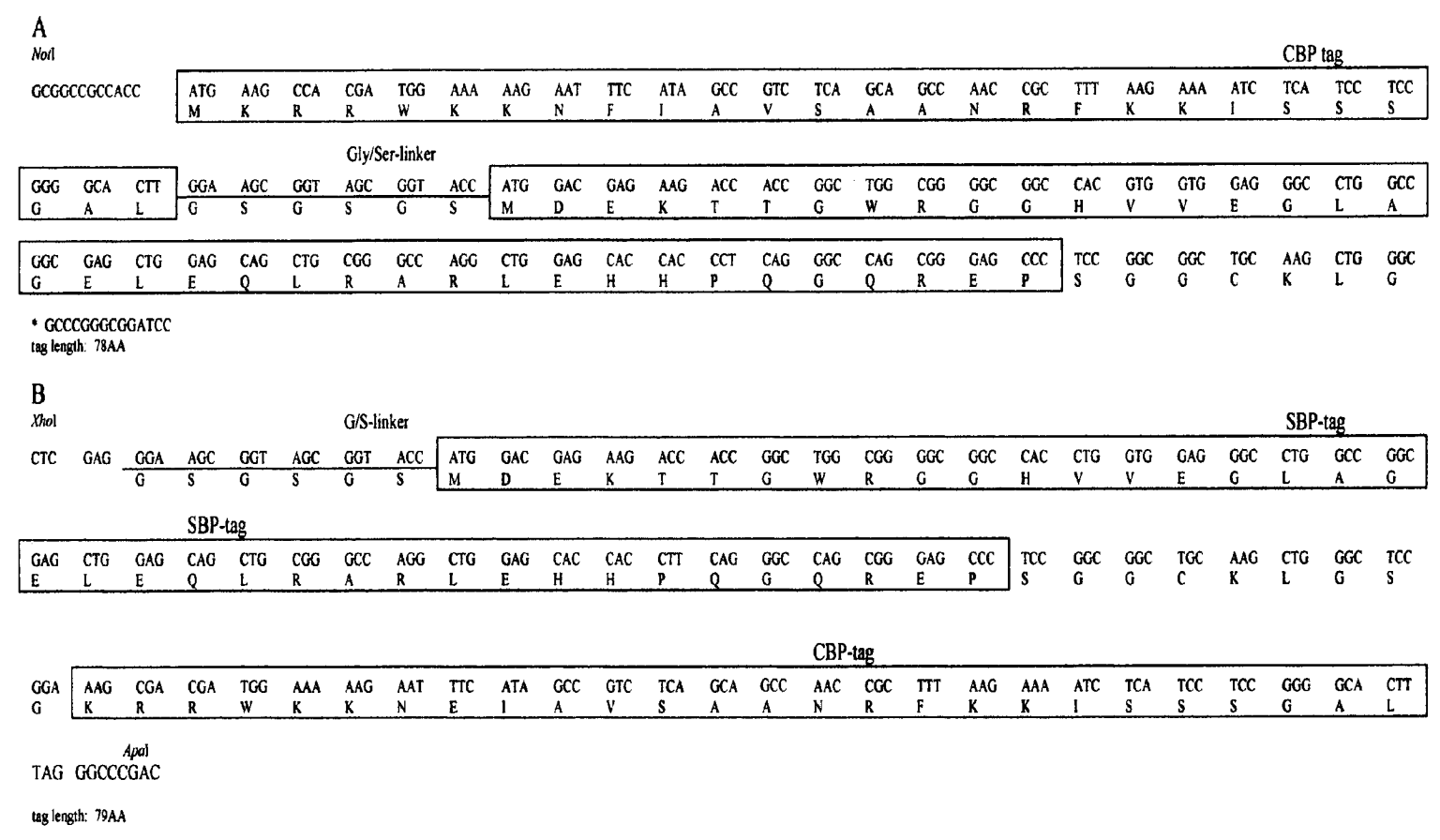

The invention provides an affinity purification tag system comprising an SBP-tag having an amino acid sequence presented in FIG. 1. A second affinity tag includes but is not limited to any of the tags described herein. The invention also provides an affinity purification tag system combining a CBP-tag with an SBP-tag. The invention also provides for an SBP having a sequence presented in any of Luo et al., 1998, J. Biotechnol., 65:225-228; Devlin et al., 1990, Science, 249:404-406; Ostergaard et al., 1995, FEBS Lett, 362:306-308; Gissel et al., 1995, J Pept Sci., 1:217-226; Schmidt et al., 1996, J Mo Biol., 255:753-766; Skerra et al., 1996, Biomol Eng., 16:79-86; Koo et al., 1998, Appl Environ Microbiol., 64:2490-2496; Aubrey et al., 2001, Biol Chem., 383:1621-1628. Preferably, the invention provides for an affinity purification tag system comprising an SBP tag and at least a second affinity tag. Other SBP tags useful according to the invention are presented in FIG. 2, in particular SB1, SB2, SB5, SB9, SB11 and SB12.

Streptavidin has traditionally been used as an affinity tag because it binds biotin with high affinity ($K_d=10^{-14}$ M) and specificity. Streptavidin will bind biotinylated compounds (such as proteins and nucleic acids) under physiological conditions and the bound compounds are subsequently eluted with biotin. Tagging the targeted protein for streptavidin purification can be achieved by several methods. Biotinylation can be directed to the tagged protein by using domains that are substrates for biotin ligases (de Boer et al., 2003, *Proc Natl Acad Sci USA*, 100:7480-7485)). However, this approach requires a biotin ligase, which has to be delivered either in vivo or in vitro (de Boer et al., supra). Alternatively, protein tags can be used that have affinity for streptavidin in the absence but not in the presence of biotin and are thus elutable. Two tags with such features have been described: streptag II (Schmidt et al., 1996, *J Mol Biol.*, 225:753-766) and the streptavidin binding peptide (SBP) (Wilson et al., 2001, *Proc Natl Acad Sci USA*, 98:3750-3755; Keefe et al., 2001, *Protein Expr Purif.*, 23:440-446; U.S. 2002/0155578 A1)). SBP has a much higher affinity for streptavidin than streptag II (Wilson et al., supra). ***

CBP has 26 residues (see FIG. 1) and is derived from the C-terminus of skeletal-muscle myosin light chain kinase, which binds calmodulin with nanomolar affinity in the presence of 0.2 mM $CaCl_2$ (Blumenthal et al., *Proc. Natl. Acad Sci USA*, 82:3187-3191). In one embodiment of the invention, CBP has the sequence presented in FIG. 1. Additional CBP sequences useful according to the invention include: bovine neuromodulin AA 37-53 KIQAS-FRGHITRKKLKG (SEQ ID NO: 1) (Hinfichsen et al., 1993, Proc. Natl. Acad Sci USA, 90:1585); calmodulin-dependent protein kinase I (CMKI) AA 294-318 SEQIKKN-FAKSKWKQAFNATAVVRHMRK (SEQ ID NO: 2); calmodulin-dependent protein kinase II (CMKII) AA 290-309 LKKFNARRKLKGAILTTMLA (SEQ ID NO: 3); and tuberous sclerosis 2 (TSC) WIARLRHIKRLRQRIC (SEQ ID NO: 4) (Noonan et al., 2002, Arch, Biochem. Biophys. 389:32).

A purification tag, according to the invention, possesses the following characteristics: (i) the interaction between the tag and the purification matrix is high affinity for example, in the range of $10^3 M^{-1}$ to $10^{14} M^{-1}$; or more (ii) binding occurs under physiological conditions, and does not disrupt the protein-protein interactions of the targeted complex; (iii) elution of the targeted complex from the purification matrix occurs under physiological conditions that do not disrupt the protein-protein interactions; (iv) the binding and elution conditions of the two purification tags are compatible with each other; and (v) the purification tag and the purification matrix have low affinity, for example, less than $10^3 M^{-1}$, for other proteins within the cell lysate to reduce non-specific background.

The invention provides for fusion proteins that are tagged with at least two adjacent tag moieties. In a preferred embodiment, a protein of interest is tagged at the N- or C-terminus with adjacent SBP and CBP tags. Combinations of any of the following tags are also useful according to the invention: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

The invention also provides for a first protein that is tagged with at least one of the following tags: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP, in combination with a binding partner or candidate binding partner that is tagged with at least one of the following tags: calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

The affinity tags may be fused in-frame to a protein of interest such that the tags are directly adjacent to each other, and/or to the protein of interest, or they may be separated from each other and/or from the protein of interest, by a linker (for example of 2-20 amino acids). The order in which the tags are fused with the polypeptide is not critical but can be chosen according to the affinity protocol to be used. Preferably, the tags are located near to the same end of the polypeptide(s). The location of the tag(s) is selected to allow for expression of an appropriate concentration of a correctly folded and processed tagged protein of interest. The tagged protein must not interfere with protein function, cell growth or cell viability.

Small peptides such as CBP or SBP can even be fused to the polypeptide(s) of interest internally (as long as the reading frame of the nucleic acid encoding either the tag or the nucleic acid of interest is maintained).

In one embodiment, at least one affinity tag, for example SBP is fused to a first protein and at least one affinity tag, for example CBP is fused to a second protein of the same complex. This strategy allows the purification of protein complexes containing two given proteins even when only a small fraction of the target proteins are associated, e.g., when large fractions remain free or bound to other complexes.

The invention provides for a method of detecting a binding partner ("target") for a protein of interest ("bait"). According to the method of the invention, a "bait" protein that comprises at least two tags is expressed in a cell with one or more "target" binding partners that comprise at least one different tag. In one embodiment, the bait comprises tandem, adjacent SBP and CBP tags and the binding partner comprises a third tag, for example a FLAG tag. The invention also provides for a binding partner that expresses at least one of any of the following tags: biotin, calmodulin binding peptide, streptavidin binding peptide, calmodulin binding peptide, streptavidin, avidin, polyhistidine tag, polyarginine tag, FLAG tag, c-myc tag, S-tag, cellulose binding domain, chitin-binding domain, glutathione S-transferase tag, Maltose-binding protein, TrxA, DsbA, hemagglutinin epitope, InaD, NorpA, and GFP.

Vectors

The invention provides for polynucleotides that can be provided in vectors and used for production of a tagged protein of interest. The tagged protein of interest is used, according to the methods of the invention, to purify a protein complex of interest, and/or to identify binding partners for the protein of interest.

A vector of the invention is designed to maintain expression of the chimeric protein and or candidate binding partner, at, or close to, its natural level. Overexpression of the protein may induce association with nonnatural binding partners. Transcriptional control sequences are therefore selected so that the chimeric protein is not over-expressed but is expressed at basal levels in the cell. For example, a protein of interest is expressed under the control of the endogenous promoter for the protein of interest. This serves to ensure that the protein is expressed in a native form. As used herein, "native form" means that a correct or relatively close to natural three-dimensional structure of the protein is achieved, i.e., the protein is folded correctly. More preferably, the protein will also be processed correctly and correctly modified at both the post-transcriptional and post-translational level. The correct folding is of great importance especially when the expressed polypeptide is a subunit of a protein complex because it will only bind to the other subunits of the complex when it is present in its native conformation. It is also possible to express mutant proteins, according to the methods of the invention. These can also have a native conformation. Such mutant proteins can, for example, be used to purify mutant complexes, i.e., complexes that contain some other mutated protein.

A vector of the invention contains a nucleic acid of interest under the control of sequences which facilitate the expression of the chimeric protein in a particular host cell or cell-free system. The control sequences comprise sequences such as a promoter, and, if necessary enhancers, poly A sites, etc. The promoter and other control sequences are selected so that the chimeric protein is preferably expressed at a basal level so that it is produced in soluble form and not as insoluble material. Preferably, the chimeric protein is also expressed in such a way as to allow correct folding for the protein to be in a native conformation. Preferably, one or more selectable markers are also present on the vector for the maintenance in prokaryotic or eukaryotic cells. Basic cloning vectors are described in Sambrook et al., Molecular Cloning, Molecular Cloning, A Laboratory Manual, Cold Spring Harbor Laboratory Press, (1989). Examples of vectors useful according to the invention include plasmids, bacteriophages, other viral vectors and the like. Vectors useful according to the invention are also presented in FIGS. 3 and 4.

In a preferred embodiment, vectors are constructed containing pre-made cassettes of an affinity tag or affinity tag combinations (for example, two or more adjacent tags, wherein a first tag is an SBP tag, for example, having the nucleotide sequence presented in FIG. 1, or two or more adjacent tags, wherein a first tag is an SBP tag and a second tag is a CBP tag) into which the nucleic acid coding the protein of interest can be inserted by means of a multiple cloning site such as a polynucleotide linker. Thus, a vector according to the invention is also one which does not contain the coding sequences for the protein of interest but contains the above-recited vector components plus one or more polynucleotide linkers with preferably unique restriction sites in such a way that the insertion of nucleic acid sequences, according to conventional cloning methods, into one of the sites in the polynucleotide linker, leads to a vector encoding the chimeric protein of the invention. Unique restriction enzyme sites located upstream and downstream of the tag or tags of the invention, facilitate cloning of a target protein of interest such that the tag or tags are located N- or C-terminally, or internally in the protein of interest.

In a further preferred embodiment, the vector comprises heterologous nucleic acid sequences in the form of two or more cassettes each comprising at least one of two different affinity tags, one of which is an SBP tag, for example, having the nucleotide sequence presented in FIG. 1, and at least one polynucleotide linker for the insertion of further nucleic acids. Alternatively, a vector of the invention comprises heterologous nucleic acid sequences in the form of two or more cassettes each comprising at least one of two different affinity tags, one of which is an SBP tag and one of which is a CBP tag. Such vectors can be used to express two subunits of a protein complex, each tagged with a different tag.

The invention provides for expression vectors that express the protein product of a gene of interest fused in frame to tandem tags. The tandem tags are fused in frame to either the N or C-terminus of the protein of interest. In one embodiment, a first tag is fused in frame to the N-terminus, and a second tag is fused in frame to the C-terminus of the protein of interest. Alternatively, one or more tags of the invention are fused internally to a protein of interest.

In a preferred embodiment, the invention provides for a CMV vector. The invention provides for regulatable expression systems that provides for expression of the chimeric protein at a level that is, preferably, equivalent to the level of expression of the endogenous protein. In one embodiment the regulatable expression system is an ecdysone regulated expression system (Complete Control, Stratagene, No.: 217468). In another embodiment, the system is regulatable due to the inclusion of aptamer sequences in the 5' untranslated region of, for example, the gene of interest (as described in Werstuck et al., 1988, *Science*, 282:296; Harvey et al., 2002, *RNA*, 8:452; Hwang et al., 1999, *Proc Natl Acad Sci USA*, 96:12997).

In another embodiment, the invention provides for a viral vector system to increase the transformation efficiency of mammalian cell lines.

Vectors useful according to the invention include CMV vectors wherein a CBP and a SBP tag are fused to the N or C terminus of the bait protein in each of the three possible reading frames. Vectors useful for expressing a CBP-SBP tagged protein of the invention are presented in FIG. 3.

Vectors useful for expressing a FLAG tagged protein of the invention are presented in FIG. 4 and are available from Stratagene.

Construction of vectors according to the invention employs conventional ligation techniques. Isolated plasmids of DNA fragments are cleaved, tailored and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art.

Gene presence, amplification and/or expression may be measured in a sample directly, for example, by conventional Southern blotting, Northern blotting to quantitate the transcription of mRNA, dot blotting (DNA or RNA analysis), PCR, RT-PCR, Q-PCR, RNase Protection assays or in situ hybridization, using an appropriately labeled probe based on a sequence provided herein. Those skilled in the art will readily envisage how these methods may be modified, if desired. Standard DNA cloning procedures are, therefore, used to introduce the N or C terminal tandem tags in frame with the coding region of the protein of interest in an appropriate expression vector.

Cells

A vector of the invention can be introduced into an appropriate host cell. These cells can be prokaryotic or eukaryotic cells, e.g., bacterial cells, yeast cells, fungi or mammalian cells, and the vector or nucleic acid can be introduced (transformed) into these cells stably or transiently by conventional methods, protocols for which can be found in Sambrook et al. (supra).

DNA may be stably incorporated into cells or may be transiently expressed using methods known in the art (see Sambrook et al., supra). Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene of interest, to monitor transfection efficiency. In one embodiment, the bait vector is introduced via infection using a viral vector such as adenoviral vectors, AAV vectors, retroviral vectors or lentiviral vectors.

Vectors of the invention can be present extrachromosomally or integrated into the host genome, and used to produce recombinant cells or organisms such as transgenic animals.

Tagged Protein

The polynucleotides of the invention are useful for production of a tagged protein of interest. The tagged protein can be tagged at the N- or C-terminus, or a combination thereof, with one or more affinity tags as described herein. The tagged protein is used to purify a complex comprising the protein of interest and/or to identify binding partners for the protein of interest.

Complex of the Invention

The invention provides for methods of detecting and isolating a complex of the invention. A complex of the invention may comprise a complex of proteins or a complex of biomolecules, as defined herein. A complex of the invention comprises a protein of interest.

As used herein, "protein of interest" means any protein for which the nucleic acid sequence is known or available, or becomes available, such that it can be cloned into a nucleic acid vector which is suitable for expression in the appropriate host cells or cell-free expression systems. For purification of a protein complex, the nucleic acid sequence of at least one of the subunits of the protein complex must be known or available.

Proteins useful according to the invention include but are not limited t0:

1) cell cycle regulatory proteins (for example cyclins, cdks, Rb, E2F, regulators of cyclins including p21,);

2) protein complexes involved in regulating intracellular transport (for example nuclear transport channels, transport into Golgi, transport into mitochondria);

3) proteins involved in the regulation of gene expression (for example transcription factors (e.g., p53, myc), transcription complexes (e.g., TATA binding protein complexes); transcriptional modulators (for example histone acetylases and histone deacetylases); components of snRNPs (involved in splice junction recognition); polyadenylation complexes; regulators of nuclear export of nucleic acids; RISC complex (components of the RNAi pathway);

4) growth factor receptors (EGFR, IGFR, FGFR);

5) regulators of the cytoskeleton (for example components of the focal adhesion complexes (paxillin, focal adhesion kinase); regulators of actin organization (racB);

6) viral proteins interacting with host proteins (for example EBNA2, EBNA1 of EBV, E1A/E1B of adenovirus, E6 and E7 of HPV);

7) proteins of pathogenic bacteria that bind to mammalian host cells; and 8) proteins in complexes that mediate cell/cell interactions (for example gap junctions (connexin).

A protein of interest useful according to the invention also includes lipoproteins, glycoproteins, phosphoproteins. Proteins or polypeptides which can be analyzed using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. Specific examples of these compounds include proinsulin (GenBank #E00011), growth hormone, dystrophin (GenBank # NM_007124), androgen receptors, insulin-like growth factor I (GenBank #NM_00875), insulin-like growth factor II (GenBank #X07868) insulin-like growth factor binding proteins, epidermal growth factor TGF-α(GenBank #E02925), TGF-β (GenBank #AW008981), PDGF (GenBank #NM_002607), angiogenesis factors (acidic fibroblast growth factor (GenBank #E03043), basic fibroblast growth factor (GenBank #NM_002006) and angiogenin (GenBank #M11567), matrix proteins (Type IV collagen (GenBank #NM_000495), Type VII collagen (GenBank #NM_000094), laminin (GenBank #J03202), phenylalanine hydroxylase (GenBank #K03020), tyrosine hydroxylase (GenBank #X05290), oncogenes (ras (GenBank #AF 22080), fos (GenBank #k00650), myc (GenBank #J00120), erb (GenBank #X03363), src (GenBank #AH002989), sis GenBank #M84453), jun (GenBank #J04111)), E6 or E7 transforming sequence, p53 protein (GenBank #AH007667), Rb gene product (GenBank #m19701), cytokine receptor, Il-1 (GenBank #m54933), IL-6 (GenBank #e04823), IL-8 (GenBank #119591), viral capsid protein, and proteins from viral, bacterial and parasitic organisms which can be used to induce an immunologic response, and other proteins of useful significance in the body.

The compounds which can be incorporated are only limited by the availability of the nucleic acid sequence for the protein or polypeptide to be incorporated. One skilled in the art will readily recognize that as more proteins and polypeptides become identified they can be integrated into the DNA constructs of the invention and used to transform or infect cells useful for producing an organized tissue according to the methods of the present invention. Therefore, a protein of interest includes the protein product of any open reading frame included in GenBank.

Protein Expression

Depending on the protein to be purified, the chimeric protein is expressed intracellularly or secreted into the culture medium. Alternatively, it might be targeted to other cell compartments such as the membrane. Depending on the protein, an appropriate method is used to extract the chimeric protein from the cells and/or medium. When a chimeric protein is expressed and targeted to a particular subcellular location, e.g., the membrane of cell organelles or the cell membrane, these organelles or the cells themselves can be purified via the binding of these membrane proteins. It is also possible to purify cells or cell organelles via proteins naturally expressed on their surface which bind to the chimeric protein of the invention.

According to the invention it is also possible to use cell-free systems for the expression of the protein of interest. These must provide all the components necessary to effect expression of proteins from the nucleic acid, such as transcription factors, enzymes, ribosomes etc. In vitro transcription and translation systems are commercially available as kits so that it is not necessary to describe these systems in detail (e.g. rabbit reticulocyte lysate systems for translation). A cell-free or in vitro system should also allow the formation of complexes.

Protein Isolation

Various extraction procedures known in the art, and known to be compatible with purification of a protein of interest are used to prepare extracts from cells or organisms expressing the tagged target protein. Cell fractionation and/or tissue dissection can facilitate purification by providing a preenrichment step or can be used to assay specifically protein complex compositions in various tissues or cell compartments.

An extraction procedure that is useful according to the invention does not interfere with the interaction of the bait and the target proteins. For example, extraction is preferably performed in the absence of strong detergents and reducing agents, or any agent that may induce protein denaturation.

A protein extract is prepared from an appropriate cell type by first exposing the cell to either mechanical and/or chemical disruption. Mechanical disruption may include electric homogenizers, blenders, "Dounce" homogenizers, and sonicators. Chemical disruption of cells usually occurs with the use of detergents that solubilize cell membranes resulting in cell lysis.

Protease inhibitors and phosphatase inhibitors are routinely added to cell lysates, at concentrations well known in the art, to prevent proteolysis. Centrifugation is performed to separate soluble from insoluble protein and membranes, and both fractions are processed separately. Nucleic acid contaminants are usually removed from the soluble protein extract by first shearing the nucleic acid polymers or treating with DNase or a combination of DNase and RNase. Protamine sulfate or polyethylene imine are added in various concentrations, known in the art, followed by centrifugation, resulting in a compact pellet of nucleic acid and protamine sulfate or polyethylene imine. This pellet is then discarded. The soluble protein extract is now ready for further processing.

The insoluble protein fraction described above can be solubilized with a variety of detergents, known in the art, and membrane proteins and analyzed.

Affinity Purification

The invention provides for a chimeric protein that comprises an affinity tag, and preferably at least two affinity tags. The presence of a second affinity tag is used to increase the purity following a second affinity chromatography step.

Methods of affinity purification useful according to the invention are well known in the art and are found on the world wide web at urich.edu/~jbell2/CHAPT3.html.

For purification according to the invention it is preferable to employ affinity chromatography using a matrix coated with the appropriate binding partner or "ligand" for the affinity tag used in that particular purification step.

A matrix material for use in affinity chromatography according to the invention has a variety of physical and chemical characteristics that give it optimal behavior. In terms of its physical properties it should have a high porosity, to allow maximum access of a wide range of macromolecules to the immobilized ligand. It should be of uniform size and rigidity to allow for good flow characteristics, and it must be mechanically and chemically stable to conditions used to immobilize the appropriate specific ligand. In terms of its chemical properties, it should have available a large number of groups that can be derivatized with the specific ligand, and it should not interact with proteins in general so that nonspecific adsorption effects are minimized.

A diverse variety of insoluble support materials are useful according to the invention, including but not limited to agarose derivatives, cellulose, polystyrene gels, cross-linked dextrans, polyacrylamide gels, and porous silicas, and beaded derivatives of agarose.

Methods of immobilizing a ligand of the invention onto a support matrix are provided on the world wide web at urich.edu/~jbell2/CHAPT3.html.

In accordance with the preferred embodiment of the invention, to purify a complex comprising a chimeric protein with two affinity tags, two affinity purification steps are carried out. Each affinity step consists of a binding step in which the extracted protein is bound via one of its affinity tags, to a support material which is covered with the appropriate binding partner for that affinity tag. Unbound substances are removed and the protein to be purified is recovered from the support material. This can be done in at least two ways. Conventional elution techniques such as varying the pH, the salt or buffer concentrations and the like depending on the tag used, can be performed Alternatively, the protein to be purified can be released from the support material by proteolytically cleaving off the affinity tag bound to the support. If the cleavage step is performed, the protein can be recovered in the form of a truncated chimeric protein or, if all affinity tags have been cleaved off, as the target polypeptide itself.

In one embodiment, biotin is added and competes for streptavidin binding sites occupied by SBP. EGTA is also added to complex with $Ca^{2+}$, thus disrupting the interaction between CBP and calmodulin. In other embodiments, other small molecules are added, and compete for binding sites on the affinity ligand, thereby dissociating bound protein complexes.

Elution conditions are preferably mild so that the interaction of the bait and the target is not disrupted. Preferably, non-physiological salt or pH conditions are avoided.

In one embodiment, non-specific binding proteins that naturally interact with calmodulin or streptavidin (for example naturally biotinylated proteins) are removed in a pre-purification step by incubation with avidin to bind biotinylated but not SBP tagged protein.

Protein Detection

Proteins associated with the tagged protein of interest are detected by a variety of methods known in the art.

Proteins are analyzed by SDS-polyacrylamide gel electrophoresis (SDS-PAGE) and stained (either by Coomassie or by silver staining). Bands of interest are excised from the gel, and analyzed by mass spectrometry (for example as described in Honey et al., supra), either directly or following in-gel digestion, for example, with trypsin.

Associated proteins can also be identified by Western blot analysis or co-immunoprecipitation.

In certain embodiments, the eluate fraction from the affinity purification step(s)) is concentrated, for example by TCA precipitation (Puig et al. supra) prior to analysis by SDS-PAGE.

Kits

The invention herein also contemplates a kit format which comprises a package unit having one or more containers of the subject vectors of the invention. The kit may also contain one or more of the following items: primers, buffers, affinity purification resins, instructions, and controls. Kits may include containers of reagents mixed together in suitable proportions for performing the methods in accordance with the invention. Reagent containers preferably contain reagents in unit quantities that obviate measuring steps when performing the subject methods.

The vectors of the kit are provided in suitable packaging means, for example in a tube, either in solution in an appropriate buffer or in a lyophilized form.

Uses

The invention provides reagents and methods for identifying one or more protein binding partners or ligands that interact, either directly or indirectly, with a protein of interest.

The invention also provides for methods of detection and/or identification of a protein complex comprising two or more proteins or biomolecules.

The invention also provides a method of analyzing the structure and/or activity of a purified complex of one or more proteins or biomolecules. In particular, the method can be used to determine the approximate stoichiometry of proteins in a given complex.

The methods of the invention are also useful for purification of a protein complex, without disruption of the complex.

The methods of the invention can also be used to identify proteins or biomolecules present in a complex.

The methods of the invention are also useful for identification of one or more binding partners for a protein of interest.

The polynucleotides of the invention are useful for producing a tagged protein of interest.

Having now generally described the invention, the same will be more readily understood through reference to the following Examples which are provided by way of illustration, and are not intended to be limiting of the present invention, unless specified.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

EXAMPLES

Example 1

Construction of a Tandem Affinity Tag Vector

The invention provides for vectors that express a tandem affinity tagged protein wherein the affinity tags are positioned either at the C- or N-terminus of a protein of interest. CMV-driven mammalian expression vectors with tandem SBP and CBP tags, that express a protein of interest wherein the tags are positioned either at the N-terminus of the C-terminus of the protein are constructed. Nucleotide and amino acid sequences of SBP and CBP tags are provided in FIG. 1. Polynucleotides and vectors useful for construction of a tandem affinity tagged protein of interest are presented in FIG. 3.

All buffers described in the following examples are described in Example 3.

The open reading frames of the transcription factors MEF2a and MEF2c (Myosin Enhancing Factor) were cloned into the CMV-driven expression vectors described above, resulting in addition of CBP and SBP-tags either at the N-terminus or at the C-terminus of the tagged protein. These constructs act as the bait to co-purify interacting proteins. MEF2a and MEF2c were chosen because their interaction has previously been demonstrated to be detectable using a CBP/proteinA-based tandem affinity purification system (Cox et al., 2002, *Biotechniques*, 33:267-270; Cox et al., 2003, *J. Biol. Chem.*, 278:15297-15303). Since members of the MEF2 family can dimerize with each other (forming homo- and hetero-dimers), MEF2a as well as MEF2c were inserted in mammalian expression vectors containing the FLAG-tag (for example as in FIG. 4) as a fusion to either the N-terminus or the C-terminus of MEF2 and MEF2c, for immunodetection. These vectors provided the "target" protein in the purification procedure. The bait vectors containing either MEF2a or MEF2c were co-transfected with the target expression vectors (either Flag-tagged MEF2a or MEF2c) into COS-7 cells (as described below). MEF2a bait protein complexed with target MEF2c and MEF2c bait protein complexed with target MEF2a were purified using the tandem affinity purification reagents and purification procedure described below. Protein complexes were characterized by Western blotting and mass spectrometry.

Example 2

Expression of a Tandemly Tagged Protein

A tandemly tagged protein of interest was expressed as follows.

COS-7 cells were grown in DMEM media with 10% FBS and antibiotics (Pen/Strep) in T175 flasks overnight to 50-60% confluency. Media was aspirated and 25 ml of fresh media was added before transfection. 30 μg of MEF2a-CBP-SBP and 30 ug of MEF2c-FLAG plasmids were diluted in 1.5 ml of serum-free DMEM media. 120 μl of Lipofectamine 2000 was diluted in 1.5 ml of serum-free DMEM media and incubated for 5 min at room temperature. The DNA and LF2000 solutions were combined and incubated for 20 min at room temperature. 3 mls of DNA-lipid complex was added to the cells and incubated at 37° C. for 48 hr. Cells were washed three times with PBS. 5 ml of ice-cold PBS was then added to each flask, and the cells were scraped and transferred to a 15 ml conical tube. The cells were centrifuged at 1500×g for 10 minutes. The PBS was aspirated and 1 ml of lysis buffer (described below) was added. Lysed cells were stored at −80° C. Cells from four to eight T175 flasks were used for each experiment.

Example 3

Purification of a Protein Complex

A protein complex comprising a tandemly tagged protein of interest and its binding partner was purified according to the following method.

All steps were performed at 4° C. Approximately $1 \times 10^7$ cells (1×T175 flask) (prepared as described in example 2) were freeze thawed for 3 cycles in 1 ml lysis buffer. The cells were centrifuged to pellet cell debris for 10 min at 16,000 g. The cleared lysates from 4-8 flasks were pooled in a fresh tube. A 5 μl sample was reserved and frozen for Western Blot analysis. To the remainder of the pooled lysate was added EDTA to a concentration of 2 mM, and β-mercaptoethanol to a concentration of 10 mM (4 μl of 0.5 M EDTA, and 0.7 μl of 14.4 M βME, for each 1000 μl of lysate) resulting in the lysates being contained in Streptavidin Binding Buffer.

100 μl of Streptavidin beads (50% slurry) for each 1 ml of lysate were washed in SBB to remove the ethanol storage buffer as follows. Beads for multiple 1 ml lysate preps were pooled and washed together in 1 ml of SBB. Beads were collected by centrifugation at 1500 g for 5 minutes. The SBB wash supernatant was removed from the beads and the beads were resuspended a second time in 1 ml of the indicated binding buffer. The beads were collected by centrifugation at 1500 g for 5 minutes and resuspended in SBB (i.e., 100 μl SBB for each 100 μl aliquot of beads required).

100 μl of washed Streptavidin beads were added to 1 ml of lysate. The tubes were rotated for 2 hr at 4° C. to allow proteins to bind to the beads. The beads were washed twice with SBB as described above. The tubes were rotated for 5 min at 4° C. to resuspend beads between centrifugations. After the final centrifugation step, SBB was removed from the pelleted beads.

100 µl of Streptavidin Elution Buffer (SEB) was added to the pelleted beads. The tubes were rotated for 30 min at 4° C. to elute protein complex/es. The beads were pelleted by centrifugation at 1500 g for 5 minutes. The supernatant containing the eluted proteins was carefully collected and transferred to a fresh tube. A 10 µl sample from the supernatant was reserved for Western Blot analysis.

2 µl of supernatant supplement (50 mM Magnesium acetate, 50 mM Imadazole, 100 mM Calcium chloride) was added per 100 µl of supernatant such that the eluted proteins were now suspended in Calmodulin Binding Buffer (CBB). An additional 900 µl of CBB was added to the eluted proteins. For each 1 ml of eluted proteins in CBB, 100 µl of Calmodulin Affinity Resin (50% slurry) was added. (Resin for multiple 1 ml preps was pooled and washed together in 1 ml of CBB. The resin was pelleted by centrifugation at 1500 g for 5 minutes and resuspended to the original volume of 100 µl in CBB. 100 µl of washed Calmodulin Affinity Resin was added per 1 ml of eluted proteins). The tubes were rotated for 2 hr at 4° C. to allow proteins to bind to the resin. The resin was washed twice with CBB as above. The tubes were rotated for 5 min at 4° C. to resuspend the resin between centrifugations. After the last centrifugation step, the binding buffer was removed from the pelleted resin.

100 µl of Calmodulin Elution Buffer (CEB) was added to the pelleted Calmodulin Affinity Resin. The tubes were rotated for 30 min at 4° C. to elute proteins. The resin was pelleted by centrifugation at 1500 g for 5 minutes. The supernatant was carefully collected and transferred to a fresh tube. This supernatant contained the affinity purified protein complex/es.

The compositions of the buffers used in the examples presented herein are described below.

Lysis Buffer:
10 mM Tris, pH 8.0
150 mM NaCl
0.1% Nonidet P-40

Add 10 µl of the protease inhibitor cocktail (Sigma, Cat.#p8340) and 10 µl of 100 mM PMSF per 1 ml of lysis buffer before use.

| Streptavidin binding buffer (SBB) | 250 ml | |
|---|---|---|
| 10 mM Tris, pH 8.0 | 2.5 ml | 1M Tris |
| 150 mM NaCl | 7.5 ml | 5M NaCl |
| 0.1% Nonidet P-40 | 2.5 ml | 10% NP40 |
| 2 mM EDTA | 1 ml | 0.5M EDTA |
| H$_2$O | to 250 ml | |
| 10 mM 2-mercaptoethanol (ME) | Add 7 µl ME per 10 ml before use | |
| Streptavidin elution buffer (SEB):<br>SBB + 2 mM biotin. | 25 ml | |
| 10 mM Tris, pH 8.0 | 0.25 ml | 1M Tris |
| 150 mM NaCl | 0.75 ml | 5M NaCl |
| 0.1% Nonidet P-40 | 0.25 ml | 10% NP40 |
| 2 mM biotin | 500 µl | 0.1M biotin |
| H$_2$O | to 25 ml | |
| 10 mM 2-mercaptoethanol | Add 7 µl ME per 10 ml before use | |
| Supernatant Supplement | 1 ml | |
| 50 mM Magnesium Acetate | 100 µl | 0.5M Magnesium Acetate |
| 50 mM Imidazole | 50 µl | 1M Imidazole |
| 100 mM Calcium chloride | 100 µl | 1M Calcium chloride |
| H$_2$O | to 1 ml | |
| Calmodulin binding buffer (CBB) | 250 ml | |
| 10 mM Tris, pH 8.0 | 2.5 ml | 1M Tris |
| 150 mM NaCl | 7.5 ml | 5M NaCl |
| 0.1% Nonidet P-40 | 2.5 ml | 10% NP40 |
| 1 mM magnesium acetate | 0.5 ml | 0.5M MgAce |
| 1 mM imidazole | 250 µl | 1M Imidazole |
| 2 mM CaCl$_2$ | 0.5 ml | 1M CaCl$_2$ |
| H$_2$O | to 250 ml | |
| 10 mM 2-mercaptoethanol | Add 7 µl ME per 10 ml before use | |
| Calmodulin elution buffer (CEB) | 25 ml | |
| 10 mM Tris, pH 8.0 | 0.25 ml | 1M Tris |
| 150 mM NaCl | 0.75 ml | 5M NaCl |
| 0.1% Nonidet P-40 | 0.25 ml | 10% NP40 |
| 1 mM magnesium acetate | 50 µl | 0.5M MgAce |
| 1 mM imidazole | 25 µl | 1M Imidazole |
| 5 mM EGTA | 250 µl | 0.5M EGTA |
| H$_2$O | to 25 ml | |
| 10 mM 2-mercaptoethanol | Add 7 µl ME per 10 ml before use | |

Example 4

Detection of a Protein Complex

A protein complex comprising a tandemly tagged protein of interest was detected.

Immunodetection

FIG. 5 represents a Western blot of MEF2c-FLAG protein isolated according to the method of the invention, using the protocol described above. The data demonstrates that SBP/CBP-tagged MEF2a forms a complex with MEF2c-FLAG and that these proteins co-purify using the streptavidin and calmodulin affinity purification resins (lanes 4 and 7, respectively), as detected by the anti-FLAG antibody.

Affinity purified, isolated MEF2c was detected with an anti-Flag antibody hybridized to samples taken from each step of the affinity purification procedure. Cos-7 cells were co-transfected with two vector constructs. The first vector was MEF 2A with N-terminal tags Streptavidin Binding Peptide (SBP) and Calmodulin Binding Peptide (CBP). The second vector was MEF 2C with a FLAG peptide as an N-terminal tag. Cell lysates were prepared as described above. Lane 1 is 10 µl of lysate from 1×10$^7$ Cos-7 cells lysed in 1 ml of buffer. This lane shows the expression of the FLAG tag in the lysate. Lane 2 is 10 µl out of 100 µl of Streptavidin Beads after incubation and elution. This lane shows the material that remains on the beads after processing. Lane 3 is 10 µl of the 1000 µl of lysate after it has been incubated with the Streptavidin beads. This lane shows the material that is not bound by the beads. Lane 4 is 10 µl out of 100 µl of elution buffer used to elute proteins from the Streptavidin beads. This lane shows the MEF2a-MEF2c protein complex that is eluted from the streptavidin beads. Lane 5 is 10 µl out of 100 µl of Calmodulin beads after incubation and elution. This lane shows the proteins that remain on the beads after processing. Lane 6 is 10 µl of 1000 µl of material after incubation with Calmodulin Beads. This lane shows the proteins that are not bound by the Calmodulin beads. Lane 7 is 17 µl out of 100 µl of elution buffer used to elute the MEF2a-MEF2c protein complex from the Calmodulin beads. This is the final affinity purified protein complex.

Detection of MEF2 and -MEF2c by Staining

Figure 6:
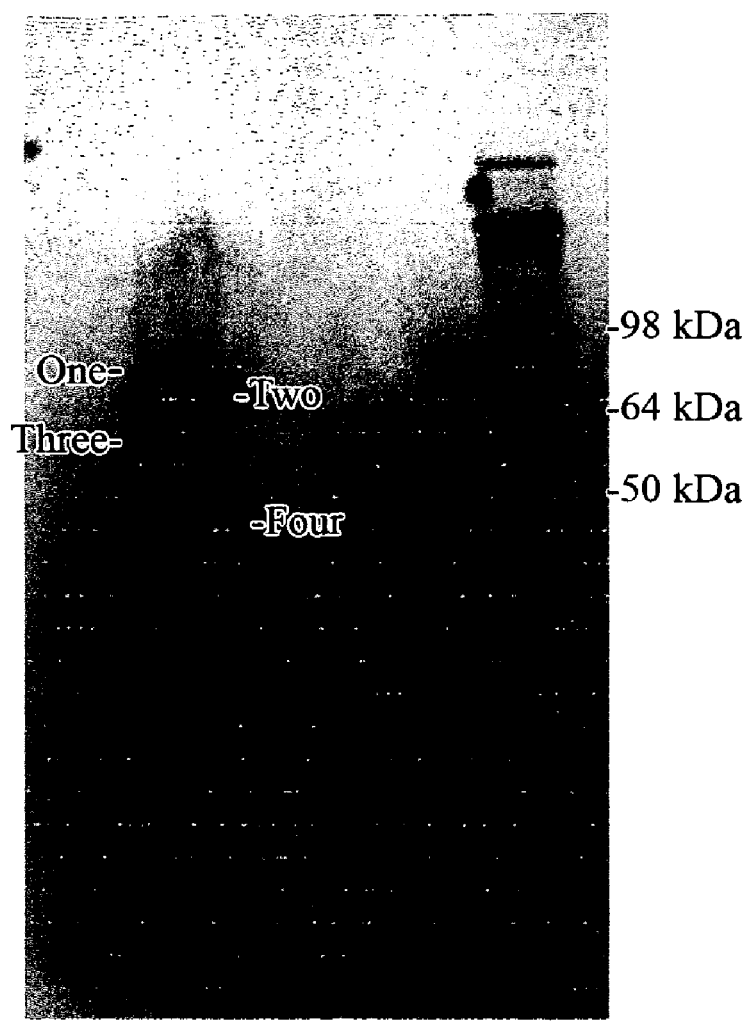
FIG. 6 is a Tris-glycine acrylamide gel of affinity purified Mef2A/Mef2c.
Figure 7:
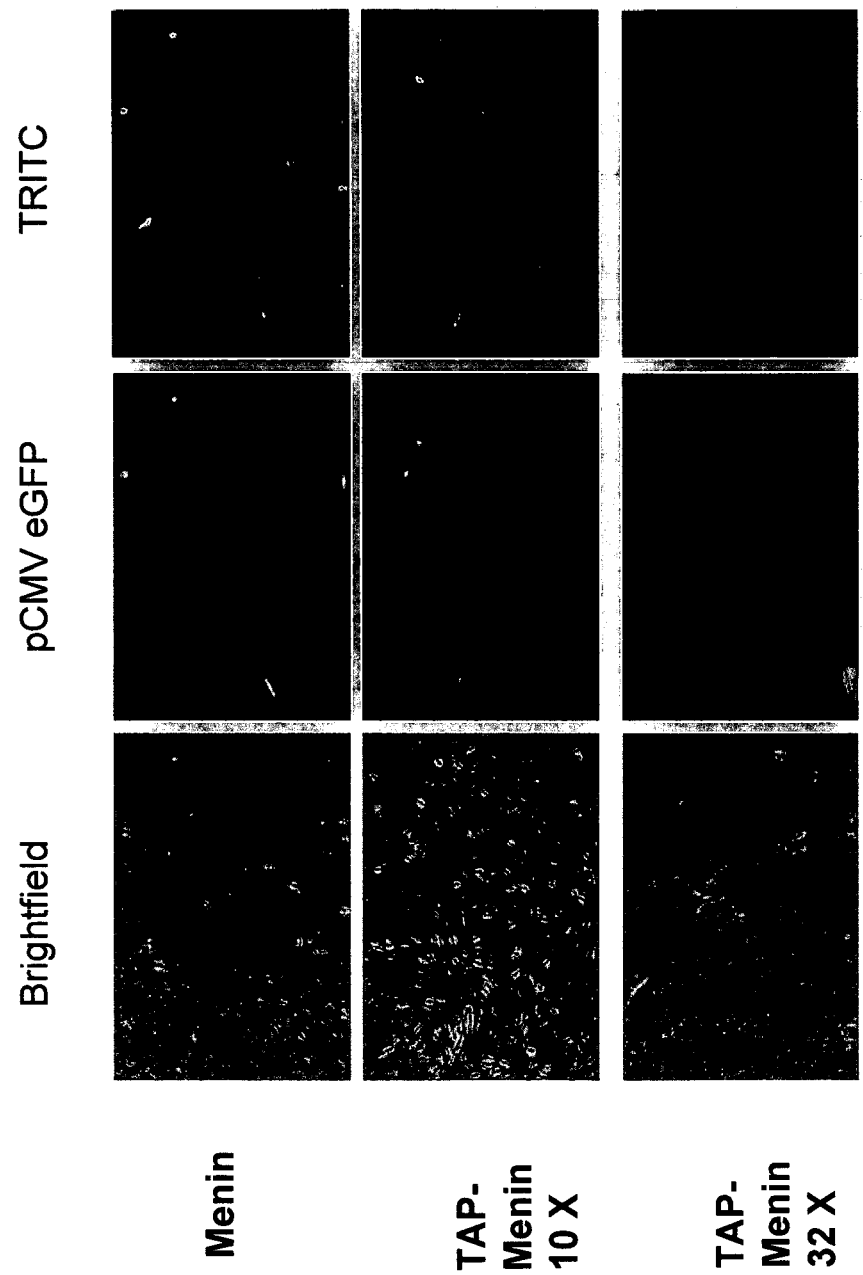

FIG. 6 shows a 4-20% Tris-glycine acrylamide gel of affinity purified MEF2a/MEF2c, stained with Commassie Brilliant Blue. The right lane shows molecular weight markers. The lane on the left is affinity purified MEF2a-SBP/CBP and MEF2c-FLAG from $5 \times 10^7$ Cos-7 cells, co-transfected with vectors expressing these tagged proteins. Protein bands labeled "One" through "Four" were excised for mass spectroscopy analysis. Mass spectrometer data analysis identifies protein in bands "One" and "Two" as MEF 2A (MOWSE scores 56 and 85, respectively). Protein band "Three" is identified as MEF 2C (MOWSE score of 78). Protein band "Four" is identified as Actin (MOWSE score 175). MOWSE scores greater than 68 represent positive identification of the protein of interest.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. An isolated polynucleotide comprising at least two different affinity tag sequences, wherein one of said two affinity tag sequences encodes streptavidin-binding peptide having a nucleotide sequence selected from the group consisting of SEQ ID No.: 5 and SEQ ID No.: 7.

2. An isolated polynucleotide comprising a gene sequence of interest and at least two affinity tag sequences, wherein said gene sequence of interest is fused in frame with each of said affinity tag sequences, and wherein one of said two affinity tag sequences encodes streptavidin-binding peptide having a nucleotide sequence selected from the group consisting of SEQ ID No.: 5 and SEQ ID No.: 7.

3. An isolated polynucleotide comprising at least two different affinity tag sequences, wherein one of said two affinity tag sequences encodes streptavidin binding peptide, and wherein one of said two affinity tag sequences encodes calmodulin binding peptide.

4. An isolated polynucleotide comprising a gene sequence of interest and at least two different affinity tag sequences, wherein said gene sequence of interest is fused in frame with each of said affinity tag sequences, and wherein one of said two affinity tag sequences encodes streptavidin binding peptide, and wherein one of said two affinity tag sequences encodes calmodulin binding peptide.

5. The isolated polynucleotide of claim 2 or 4, wherein each of said tags are adjacent to the 5' end of the target gene.

6. The isolated polynucleotide of claim 2 or 4, wherein each of said tags are adjacent to the 3' end of the gene.

7. A vector comprising the isolated polynucleotide of claim 1, 2, 3 or 4.

8. An isolated host cell comprising the vector of claim 5.

9. A composition comprising the isolated polynucleotide of claim 1, 2, 3 or 4.

10. A chimeric protein comprising at least two different affinity tags, wherein one of said affinity tags is streptavidin binding peptide, having the sequence selected from the group consisting of SEQ ID No.: 6 and SEQ ID No.: 8.

11. A chimeric protein comprising a protein of interest fused in frame to at least two different affinity tags, wherein one of said affinity tags is streptavidin binding peptide, having the sequence selected from the group consisting of SEQ ID No.: 6 and SEQ ID No.: 8.

12. A chimeric protein comprising at least two different affinity tags, wherein one of said affinity tags is streptavidin binding peptide and wherein one of said affinity tags is calmodulin binding peptide.

13. A chimeric protein comprising a protein of interest fused in frame to at least two different affinity tags, wherein one of said affinity tags is streptavidin binding peptide, and wherein one of said affinity tags is calmodulin binding peptide.

14. The chimeric protein of claim 11 or 12 wherein each of said affinity tags are adjacent to the N-terminus of the protein of interest.

15. The chimeric protein of claim 11 or 12 wherein each of said affinity tags are adjacent to the C-terminus of the protein of interest.

16. A composition comprising the chimeric protein of claim 10, 11, 12 or 13.

17. A method of detecting or isolating one or more binding partners for a protein encoded by a gene of interest, comprising the steps:

cloning a gene sequence of interest into a vector, wherein said gene sequence of interest is fused in frame with at least two different affinity tag sequences, and wherein one of said at least two affinity tag sequences encodes streptavidin binding peptide having the amino acid sequence selected from the group consisting of SEQ ID No.: 5 and SEQ ID No.: 7, introducing said vector into an isolated host cell that comprises at least one candidate-binding partner for said protein product of said gene of interest;

allowing said protein product of said gene sequence of interest and said candidate binding partner to form a complex in the cell;

isolating said complex by
a) lysing the cells; and
b) performing at least one round of affinity purification and;

detecting said protein complex.

18. A method of detecting or isolating one or more binding partners for a protein encoded by a gene sequence of interest, comprising the steps:

cloning a gene sequence of interest into a vector, wherein said gene sequence of interest is fused in frame with at least two different affinity tag sequences, and wherein one of said at least two affinity tag sequences encodes streptavidin binding peptide, and wherein one of said at least two affinity tag sequences encodes calmodulin binding peptide;

introducing said vector into an isolated host cell that comprises at least one candidate-binding partner for said protein product of said gene sequence of interest;

allowing said protein product of said gene of interest and said candidate binding partner to form a complex in the cell;

isolating said complex by
a) lysing the cells; and
b) performing at least one round of affinity purification and;

detecting said protein complex.

19. The method of claim 17 or 18 wherein said cell comprises a vector that expresses at least one candidate binding partner for said protein product of interest.

20. The method of claim 17 or 18 wherein said candidate binding partner for said protein product of interest comprises an affinity tag.

21. A method of detecting or isolating a protein complex comprising the steps of: cloning a gene sequence of interest into a vector, wherein said gene sequence of interest is fused in frame with at least two different affinity tag sequences, and wherein one of said at least two affinity tag sequences encodes streptavidin binding peptide having the amino acid sequence selected from the group consisting of SEQ ID No.: 6 and SEQ ID No.: 8;

introducing said vector into an isolated host cell that expresses at least one protein-binding partner for said protein product of said gene sequence of interest;

allowing said protein product of said gene sequence of interest and said protein binding partner to form a complex in the cell;

isolating said complex by a) lysing the cells; and b) performing at least one round of affinity purification; and detecting said protein complex.

22. A method of detecting or isolating a protein complex comprising the steps of: cloning a gene sequence of interest into a vector, wherein said gene sequence of interest is fused in frame with at least two different affinity tag sequences, and wherein one of said at least two affinity tag sequences encodes streptavidin binding peptide, and wherein one of said at least two affinity tag sequences encodes calmodulin binding peptide;

introducing said vector into an isolated host cell that expresses at least one protein-binding partner for said protein product of said gene sequence of interest;

allowing said protein product of said gene sequence of interest and said protein binding partner to form a complex in the cell;

isolating said complex by a) lysing the cells; and b) performing at least one round of affinity purification and;

detecting said protein complex.

23. The method of claim 21 or 22 wherein said cell comprises a vector that expresses at least one candidate binding partner for said protein product of interest.

24. The method of claim 21 or 22, wherein said candidate binding partner comprises an affinity tag.

25. The method of claim 17, 18, 21 or 22, wherein said complex is isolated by performing at least two successive rounds of affinity purification.

26. A kit for isolating a protein complex or identifying one or more binding partners for a protein, comprising the vector of claim 7, and packaging means.

27. The kit of claim 26, further comprising a purification resin.

\* \* \* \* \*

SEQUENCE LISTING

```
<160> NUMBER OF SEQ ID NOS: 32

<210> SEQ ID NO 1
<211> LENGTH: 17
<212> TYPE: PRT
<213> ORGANISM: Bos taurus

<400> SEQUENCE: 1

Lys Ile Gln Ala Ser Phe Arg Gly His Ile Thr Arg Lys Lys Leu Lys
1               5                   10                  15

Gly

<210> SEQ ID NO 2
<211> LENGTH: 28
<212> TYPE: PRT
<213> ORGANISM: Artificial sequence
<220> FEATURE:
<223> OTHER INFORMATION: calmodulin-dependent protein kinase I (CMKI)
      AA 294-318

<400> SEQUENCE: 2

Ser Glu Gln Ile Lys Lys Asn Phe Ala Lys Ser Lys Trp Lys Gln Ala
1               5                   10                  15

Phe Asn Ala Thr Ala Val Val Arg His Met Arg Lys
            20                  25

<210> SEQ ID NO 3
<211> LENGTH: 20
<212> TYPE: PRT
<213> ORGANISM: Artificial sequence
<220> FEATURE:
<223> OTHER INFORMATION: calmodulin-dependent protein kinase II (CMKII)
      AA 290-309

<400> SEQUENCE: 3

Leu Lys Lys Phe Asn Ala Arg Arg Lys Leu Lys Gly Ala Ile Leu Thr
1               5                   10                  15

Thr Met Leu Ala
            20

<210> SEQ ID NO 4
<211> LENGTH: 16
<212> TYPE: PRT
<213> ORGANISM: Homo sapiens

<400> SEQUENCE: 4

Trp Ile Ala Arg Leu Arg His Ile Lys Arg Leu Arg Gln Arg Ile Cys
```

<210> SEQ ID NO 5
<211> LENGTH: 260
<212> TYPE: DNA
<213> ORGANISM: Artificial sequence
<220> FEATURE:
<223> OTHER INFORMATION: DNA sequence coding CBP/SBP tandem affinity
tags fused to the N-terminus of the bait protein

<400> SEQUENCE: 5

```
gcggccgcca ccatgaagcg acgatggaaa aagaatttca tagccgtctc agcagccaac    60
cgctttaaga aaatctcatc ctccggggca cttggaagcg gtagcggtac catgacgag    120
aagaccaccg gctggcgggg cggccacgtg gtggagggcc tggccggcga gctggagcag   180
ctgcgggcca ggctggagca ccaccctcag ggccagcggg agccctccgg cggctgcaag   240
ctgggcgccc gggcggatcc                                                260
```

<210> SEQ ID NO 6
<211> LENGTH: 78
<212> TYPE: PRT
<213> ORGANISM: Artificial sequence
<220> FEATURE:
<223> OTHER INFORMATION: CBP/SBP tandem affinity tags fused to the
N-terminus of the bait protein

<400> SEQUENCE: 6

```
Met Lys Arg Arg Trp Lys Lys Asn Phe Ile Ala Val Ser Ala Ala Asn
1               5                   10                  15

Arg Phe Lys Lys Ile Ser Ser Ser Gly Ala Leu Gly Ser Gly Ser Gly
            20                  25                  30

Ser Met Asp Glu Lys Thr Thr Gly Trp Arg Gly Gly His Val Val Glu
        35                  40                  45

Gly Leu Ala Gly Glu Leu Glu Gln Leu Arg Ala Arg Leu Glu His His
    50                  55                  60

Pro Gln Gly Gln Arg Glu Pro Ser Gly Gly Cys Lys Leu Gly
65                  70                  75
```

<210> SEQ ID NO 7
<211> LENGTH: 254
<212> TYPE: DNA
<213> ORGANISM: Artificial sequence
<220> FEATURE:
<223> OTHER INFORMATION: DNA sequence coding CBP/SBP tandem affinity
tags fused to the C-terminus of the bait protein

<400> SEQUENCE: 7

```
ctcgagggaa gcggtagcgg taccatggac gagaagacca ccggctggcg gggcggccac    60
gtggtggagg gcctggccgg cgagctggag cagctgcggg ccaggctgga gcaccaccct   120
cagggccagc gggagccctc cggcggctgc aagctgggct ccggaaagcg acgatggaaa   180
agaatttca tagccgtctc agcagccaac cgctttaaga aaatctcatc ctccggggca    240
ctttagggcc cgac                                                     254
```

<210> SEQ ID NO 8
<211> LENGTH: 79
<212> TYPE: PRT
<213> ORGANISM: Artificial sequence
<220> FEATURE:
<223> OTHER INFORMATION: CBP/SBP tandem affinity tag fused to the
C-terminus of the bait protein

<400> SEQUENCE: 8

```
Gly Ser Gly Ser Gly Ser Met Asp Glu Lys Thr Thr Gly Trp Arg Gly
1               5                   10                  15
Gly His Val Val Glu Gly Leu Ala Gly Glu Leu Glu Gln Leu Arg Ala
            20                  25                  30
Arg Leu Glu His His Pro Gln Gly Gln Arg Glu Pro Ser Gly Gly Cys
        35                  40                  45
Lys Leu Gly Ser Gly Lys Arg Arg Trp Lys Lys Asn Phe Ile Ala Val
    50                  55                  60
Ser Ala Ala Asn Arg Phe Lys Lys Ile Ser Ser Ser Gly Ala Leu
65                  70                  75
```

<210> SEQ ID NO 9
<211> LENGTH: 101
<212> TYPE: PRT
<213> ORGANISM: Artificial sequence
<220> FEATURE:
<223> OTHER INFORMATION: SBP sequence (SB1)

<400> SEQUENCE: 9

```
Met Asp Glu Lys Thr His Cys Thr Ile Ser Met Asn Gly Ala Val Pro
1               5                   10                  15
Leu Val Pro His His His Pro Gln Gly Asp Pro Leu Arg Leu Leu His
            20                  25                  30
Arg Pro Gln Pro Ala Leu Leu Val Arg His Pro Gln Gly Asp Leu Val
        35                  40                  45
Ala Leu Val Glu His His Glu Gly Val Asp Arg Gly Leu Val Ala Leu
    50                  55                  60
Pro Glu Leu His Ala Glu Glu Leu Gly Glu Pro Val Gly Asp Leu Val
65                  70                  75                  80
Gln Gly Pro Val Glu Gln Val Gln Gly Val Val Asp Ala Leu Val Trp
                85                  90                  95
Arg Leu Pro Pro Ser
            100
```

<210> SEQ ID NO 10
<211> LENGTH: 101
<212> TYPE: PRT
<213> ORGANISM: Artificial sequence
<220> FEATURE:
<223> OTHER INFORMATION: SBP sequence (SB2)

<400> SEQUENCE: 10

```
Met Asp Glu Lys Thr His Cys Phe His Pro Gly Asp His Leu Val Arg
1               5                   10                  15
Leu Val Glu Glu Leu Gln Ala Leu Ala Glu Gly Leu Gln Arg Gln Gly
            20                  25                  30
Gly Arg Gln Pro His Arg Leu Pro Arg Arg Pro His His Leu Gln
        35                  40                  45
Leu Leu Leu Asp Glu Ala His Pro Gln Ala Gly Pro Leu Arg Glu Arg
    50                  55                  60
Ala His Gln Val Asp Gly Arg Leu Leu Gln His His Pro Gln Gly
65                  70                  75                  80
Asp Arg Leu Leu Gln Gln Pro Gln Asp His Pro Leu Glu Leu Val Trp
                85                  90                  95
Arg Leu Pro Pro Ser
            100
```

```
<210> SEQ ID NO 11
<211> LENGTH: 101
<212> TYPE: PRT
<213> ORGANISM: Artificial sequence
<220> FEATURE:
<223> OTHER INFORMATION: SBP sequence (SB3)

<400> SEQUENCE: 11

Met Thr Arg Arg Pro Thr Ala Ser Ser Ser Cys Val Arg His Leu
1               5                   10                  15

Leu Leu Arg Gln Gly Glu His Gly His Gln Ala Leu Glu Asp Arg Asp
            20                  25                  30

Lys Ala Arg His Val Arg Leu Val Glu Gly Asp Val Glu Val Leu Gly
        35                  40                  45

Gly Leu Asp Arg Leu Ala Arg Ala Arg His Glu Ala Leu His Pro Gln
    50                  55                  60

Ala Gly Leu Val His Leu Pro Leu His Gly Gly Asp Leu Gly Gly His
65                  70                  75                  80

Leu Arg Leu Val Leu Glu Ala His Pro Gln Gly Asp Arg Leu Gly Leu
                85                  90                  95

Ala Val His His His
            100

<210> SEQ ID NO 12
<211> LENGTH: 102
<212> TYPE: PRT
<213> ORGANISM: Artificial sequence
<220> FEATURE:
<223> OTHER INFORMATION: SBP sequence (SB4)

<400> SEQUENCE: 12

Met Asp Glu Lys Thr His Trp Gly Ile Ser Thr Trp Arg Gly Glu Pro
1               5                   10                  15

Leu Leu His His Pro Gln Ala Gly Arg Leu Pro Leu Asp Arg Arg Arg
            20                  25                  30

Ala Arg His Arg Arg Ile Leu Gly Ala Glu Pro Gly Gly Val Asp His
        35                  40                  45

Gly Leu Arg Leu Glu Leu Leu Asp Asp His Arg Pro Leu Val Pro Asp
    50                  55                  60

His His Pro Gln Arg Gly Pro Leu Gln Arg Gly Asp Leu Pro Gln Val
65                  70                  75                  80

Val Pro Leu Val Arg Leu Arg His Ala His Val Leu Gly Leu Gly Leu
                85                  90                  95

Ala Ala Ala Thr Ile Thr
            100

<210> SEQ ID NO 13
<211> LENGTH: 102
<212> TYPE: PRT
<213> ORGANISM: Artificial sequence
<220> FEATURE:
<223> OTHER INFORMATION: SBP sequence (SB5)

<400> SEQUENCE: 13

Met Asp Glu Lys Thr His Trp Val Asn Val Tyr His Pro Gln Gly Asp
1               5                   10                  15

Leu Leu Val Arg Gly His Gly His Asp Val Glu Ala Leu His Asp Gln
            20                  25                  30

Gly Leu His Gln Leu Asp Leu Leu Val Gly Pro Pro Glu Val Val
```

```
                35                  40                  45
Arg Ala Leu Arg Gly Glu Val Leu Gly Gly Leu Arg Arg Leu Val Pro
     50                  55                  60

Leu Asp His Pro Gln Gly Glu Ala Leu Asp Gln Ala Arg Gln Arg Pro
 65                  70                  75                  80

Gln His Leu Leu Glu Leu His His Arg Ala Leu Pro Pro Ala Leu Val
                 85                  90                  95

Trp Arg Leu Pro Pro Ser
            100
```

<210> SEQ ID NO 14
<211> LENGTH: 102
<212> TYPE: PRT
<213> ORGANISM: Artificial sequence
<220> FEATURE:
<223> OTHER INFORMATION: SBP sequence (SB6)

<400> SEQUENCE: 14

```
Met Asp Glu Lys Thr His Trp Leu Asn Asn Phe Glu Glu Leu Leu Ala
 1               5                  10                  15

Arg Leu Asp Gly Leu Arg Glu Gly Glu Asp His Pro Leu Val Leu Arg
             20                  25                  30

His His Pro Gln Gly Asp Gly Leu Leu Asp Gln Pro Leu Gly Arg His
             35                  40                  45

Arg Ala Leu Asp Gly Glu Val Arg Glu Gly Asp Arg Pro Leu Asp Gln
     50                  55                  60

Gly Gly Glu Glu Asp Leu Gly Ala Leu Val Asp Asp Gly Glu Val
 65                  70                  75                  80

Leu Asp Gly Leu Val His Val Gly Val His Val His Asp Pro Leu Val
                 85                  90                  95

Cys Gly Cys His His His
            100
```

<210> SEQ ID NO 15
<211> LENGTH: 101
<212> TYPE: PRT
<213> ORGANISM: Artificial sequence
<220> FEATURE:
<223> OTHER INFORMATION: SBP sequence (SB7)

<400> SEQUENCE: 15

```
Met Asp Glu Lys Thr His Trp Phe Gly Thr Leu Asn Ser Phe Pro Thr
 1               5                  10                  15

His Trp Met Ser Ala Val Gly Asn Gly Lys Ile Asp Cys Ser Phe Asn
             20                  25                  30

Met Asn Leu Ser Leu Asn His Trp Leu Ser Ser Gly His Pro Asp Gly
             35                  40                  45

Ala Leu Asp Asp Gln Leu His Pro Gln Gly Asp Ala Leu Val Gly Arg
     50                  55                  60

Asp Asp Gly Val Val Gln Ala Leu Arg Leu Glu Gly Gln His Gln His
 65                  70                  75                  80

Arg Arg Leu Ala Gln Arg Arg Ala Asp Arg His Arg Gln Leu Val Trp
                 85                  90                  95

Arg Leu Pro Pro Ser
            100
```

<210> SEQ ID NO 16
<211> LENGTH: 102

```
<212> TYPE: PRT
<213> ORGANISM: Artificial sequence
<220> FEATURE:
<223> OTHER INFORMATION: SBP sequence (SB8)

<400> SEQUENCE: 16

Met Asp Glu Lys Thr His Cys Thr Ile Glu Leu Asn Phe Ser Phe Thr
1               5                   10                  15

His Trp Lys Leu His His Pro Gln Gly Asp Ala Leu Leu Asp Asp
            20                  25                  30

Gly Val Arg Pro His His Pro Leu Ala Asp Glu Gly Gly Gly Leu Asp
        35                  40                  45

Gln Gly Leu Gly His Arg Arg Gly Val Val Ala Glu Arg Leu Ala Arg
    50                  55                  60

Arg Asp Pro Glu Val Leu Glu Gly Leu Val Glu Arg His Arg Gly Leu
65                  70                  75                  80

Val Pro Arg Leu Arg His Gly Gly Glu Arg His Ala Glu Pro Leu Val
                85                  90                  95

Trp Arg Leu Pro Pro Ser
            100

<210> SEQ ID NO 17
<211> LENGTH: 102
<212> TYPE: PRT
<213> ORGANISM: Artificial sequence
<220> FEATURE:
<223> OTHER INFORMATION: SBP sequence (SB9)

<400> SEQUENCE: 17

Met Asp Glu Lys Thr His Cys Asn Thr Gly Leu Tyr Asp Gly Ala Ala
1               5                   10                  15

Asp Cys Phe Asn Glu Leu Asn Lys Asp Val Ala Pro Leu Val Glu Gly
            20                  25                  30

Arg His Asp Leu Val Glu Gly Leu Leu Glu Arg His Pro Gln Gly
        35                  40                  45

Asp Pro Leu Val Ala His Arg Gln Leu Val His Pro Leu Leu Gly
    50                  55                  60

Arg Gly Glu Arg His Arg Arg Ala Leu Val Pro Gln Gln Glu His Gln
65                  70                  75                  80

Pro His Arg Leu Gln Pro Val Val Asp Leu Gly Arg Arg Leu Val
                85                  90                  95

Trp Arg Leu Pro Pro Ser
            100

<210> SEQ ID NO 18
<211> LENGTH: 103
<212> TYPE: PRT
<213> ORGANISM: Artificial sequence
<220> FEATURE:
<223> OTHER INFORMATION: SBP sequence (SB10)

<400> SEQUENCE: 18

Met Asp Glu Lys Thr His Trp His Glu Arg Ala Gln Glu Leu Val Gly
1               5                   10                  15

Gly Leu Leu Leu His Asp His Pro Gln Arg Leu Leu Leu Glu Pro Arg
            20                  25                  30

Gly Pro Arg Pro Leu Arg Gly Leu Val His Glu Arg Gly His Gln Pro
        35                  40                  45

Gln Pro Leu Ala Gly Arg Val Glu Glu Ala Asp Gly Gly Leu Leu Arg
```

```
                    50                  55                  60
Asp Gly Gly Gly Glu Leu Glu Pro Leu Val Arg Glu Gly Glu Asp His
 65                  70                  75                  80

Leu Glu Pro Leu Asp Asp Glu Leu Asp Ala Gly Pro Arg Gly Leu Val
                 85                  90                  95

Trp Arg Leu Pro His His His
            100

<210> SEQ ID NO 19
<211> LENGTH: 102
<212> TYPE: PRT
<213> ORGANISM: Artificial sequence
<220> FEATURE:
<223> OTHER INFORMATION: SBP sequence (SB11)

<400> SEQUENCE: 19

Met Asp Glu Lys Thr His Trp His Glu Arg Val His His Leu Ala Asp
 1               5                  10                  15

Gly Leu Glu Gln His Pro Gln Gly Gln Arg Arg Pro Leu Val Glu Arg
                20                  25                  30

His Arg Gln Val Pro Arg Gly Leu Val Arg Glu Leu Gln His Glu Gly
            35                  40                  45

Leu Pro Leu Glu His Pro Ala Gly Val His Val Ile Arg Leu His Gln
        50                  55                  60

Gly Asp Arg Asp Val Asp Gly Leu Val Asp Gly His Gly Arg Asp
 65                  70                  75                  80

Val Arg Gly Leu Glu Arg Val Gly Asp Gly Pro His Arg Leu Val
                85                  90                  95

Trp Arg Leu Pro Pro Ser
            100

<210> SEQ ID NO 20
<211> LENGTH: 101
<212> TYPE: PRT
<213> ORGANISM: Artificial sequence
<220> FEATURE:
<223> OTHER INFORMATION: SBP sequence (SB12)

<400> SEQUENCE: 20

Met Asp Lys Asp Pro Leu Leu Glu Glu Leu Glu Leu Arg Glu Arg
 1               5                  10                  15

Leu Val His His Pro Gln Gly Gly Leu Leu Pro Leu Arg Gly Gln Val
                20                  25                  30

Gly His Asp Ala Glu Arg Leu Gly Ala Glu Val Asp Asp Leu Arg Gly
            35                  40                  45

Gly Leu Leu Asp Glu Pro Gln Arg Ala Val Ala Gly Leu His His Val
        50                  55                  60

Pro His Arg Val Gly Gln Arg Leu Val His Glu Val Arg Glu Leu Asp
 65                  70                  75                  80

Glu Gly Leu Leu Asp Gln Arg Asp Leu Arg Gln Arg Leu Val Trp
                85                  90                  95

Arg Leu Pro Pro Ser
            100

<210> SEQ ID NO 21
<211> LENGTH: 102
<212> TYPE: PRT
<213> ORGANISM: Artificial sequence
<220> FEATURE:
```

-continued

<223> OTHER INFORMATION: SBP sequence (SB13)

<400> SEQUENCE: 21

```
Met Glu Arg Glu Asp Pro Leu Asp Glu Gln Leu Arg Glu Leu Arg Glu
1               5                   10                  15

Ala Leu Val Asp His Pro Gln Gly Gly Ala Gln Ala Leu His Arg His
            20                  25                  30

Asp Gly Gly Glu His Val Pro Leu Arg Arg Val Gln His Arg Leu Gln
        35                  40                  45

Pro Gly Leu Gln His His Leu Glu Pro Gln Pro Leu Gly Leu Leu Gly
    50                  55                  60

Glu Leu Gln Ala Arg Leu Gln Pro Leu Ala Gly Glu His Glu Gly Asp
65                  70                  75                  80

Gly Ala Gly Leu Gln Arg Val Pro Gly His Gln Gly Arg Arg Leu Val
                85                  90                  95

Trp Arg Leu Pro Pro Ser
            100
```

<210> SEQ ID NO 22
<211> LENGTH: 101
<212> TYPE: PRT
<213> ORGANISM: Artificial sequence
<220> FEATURE:
<223> OTHER INFORMATION: SBP sequence (SB14)

<400> SEQUENCE: 22

```
Met Asp Glu Lys Thr His Arg Thr Leu Ser Val Ser Leu Ser Phe Asn
1               5                   10                  15

Asp Trp Leu Gly Gln Thr Lys Ala Cys Trp Arg Leu Val Glu Gly Leu
            20                  25                  30

His Gly His Pro Gln Gly Leu Val Arg Glu His Glu Val Asp Val Leu
        35                  40                  45

Pro Leu Ala Glu Glu Val Gln Gln Val Val Gly Gly Leu Ala Asp Gly
    50                  55                  60

Val Glu Gln Pro Gly Gly Gly Leu Leu His Arg Ala Gln Arg Val Asp
65                  70                  75                  80

His Pro Leu Pro Asp His Ala Gly Gln Val Leu Gly Arg Leu Val Trp
                85                  90                  95

Arg Leu Pro Pro Ser
            100
```

<210> SEQ ID NO 23
<211> LENGTH: 101
<212> TYPE: PRT
<213> ORGANISM: Artificial sequence
<220> FEATURE:
<223> OTHER INFORMATION: SBP sequence (SB15)

<400> SEQUENCE: 23

```
Met Asp Glu Lys Thr His Trp Leu Glu Asp Leu Lys Gly Val Leu Lys
1               5                   10                  15

Asp Cys Leu Lys Asp Leu Met Asp Phe Thr Lys Asp Cys Arg Ser Pro
            20                  25                  30

Arg Val Gln Pro Gln Pro Leu Leu His His Asp Arg Gly Glu Pro Val
        35                  40                  45

Pro Leu Leu Arg Glu Ala Gly Arg Asp Leu Gly Gly Leu Gly Pro Arg
    50                  55                  60

Ala Pro Arg Gln Ala Arg Pro Leu His His Gly Arg His Asp Leu His
```

```
                65                  70                  75                  80
Glu Pro Leu Val Leu Gln Asp His Pro Gln Gly Gly Pro Leu Val Cys
                    85                  90                  95

Gly Cys His His His
            100

<210> SEQ ID NO 24
<211> LENGTH: 102
<212> TYPE: PRT
<213> ORGANISM: Artificial sequence
<220> FEATURE:
<223> OTHER INFORMATION: SBP sequence (SB16)

<400> SEQUENCE: 24

Met Asp Glu Lys Thr His Trp Val Leu Gln Leu His Pro Gln Gly Asp
1               5                   10                  15

Arg Leu Gly Pro Arg His Gly Gly Asp Asp Val Arg Leu Val Gly Gln
                20                  25                  30

Gly Glu Gly Val Leu Glu Gly Leu Asp Gly Arg Pro Arg Arg Arg Arg
            35                  40                  45

His Arg Leu Pro Arg Glu Asp Glu His Arg Val Arg Ala Leu Val Asp
        50                  55                  60

Gln Val Arg Asp Leu Ala Glu Arg Leu Val Glu Val Asp Gly Gly
65                  70                  75                  80

Val Glu Ala Leu Arg His Leu Gly Leu Pro Gln Asp Glu Pro Arg Ser
                85                  90                  95

Gly Gly Cys His His His
            100

<210> SEQ ID NO 25
<211> LENGTH: 102
<212> TYPE: PRT
<213> ORGANISM: Artificial sequence
<220> FEATURE:
<223> OTHER INFORMATION: SBP sequence (SB17)

<400> SEQUENCE: 25

Met Asp Glu Lys Thr His Trp Val Gly Asp Leu Gln Glu Pro Leu Gly
1               5                   10                  15

Pro Leu His Gly Gly Val Gly Glu Val Pro Gly Gly Leu Val Leu Arg
                20                  25                  30

His His Pro Gln Arg Asp Arg Leu Val Asp Gly Val Gly Pro His Gly
            35                  40                  45

Arg Ala Leu Ala Arg Arg Pro His Arg Val Val Glu Gly Leu His His
        50                  55                  60

Leu Leu Gln Arg Gly Gly Glu Arg Leu Pro Pro Asp Gly Pro Arg Gln
65                  70                  75                  80

Leu Gly Leu Leu Gly Gly Glu Leu Asp Arg Ala Asp Pro Ala Leu Val
                85                  90                  95

Trp Arg Leu Pro Pro Ser
            100

<210> SEQ ID NO 26
<211> LENGTH: 101
<212> TYPE: PRT
<213> ORGANISM: Artificial sequence
<220> FEATURE:
<223> OTHER INFORMATION: SBP sequence (SB18)

<400> SEQUENCE: 26
```

Met Asp Glu Lys Thr His Cys Ala Val Asn Val Asn Val Gly Leu Thr
1               5                   10                  15

His Trp Cys His Arg Val Ala His Leu Gln Pro Leu Asp Pro His Pro
            20                  25                  30

Gln Gly Asp His Leu Arg Leu Glu Pro Leu Gly His Ala Leu Val Asp
        35                  40                  45

Pro Leu Val Gln Gly Val Glu Val Val Arg Pro Leu Gln Leu Asp
    50                  55                  60

Val Gly Val Gln Arg Val Ala Leu Val Glu Gln Val Ala Glu Val Gly
65                  70                  75                  80

Glu Gly Leu Asp His Glu Ala Gly Gln Ala His Gly Ala Leu Val Trp
                85                  90                  95

Arg Leu Pro Pro Ser
            100

<210> SEQ ID NO 27
<211> LENGTH: 101
<212> TYPE: PRT
<213> ORGANISM: Artificial sequence
<220> FEATURE:
<223> OTHER INFORMATION: SBP sequence (SB19)

<400> SEQUENCE: 27

Met Asp Glu Lys Thr Thr Gly Trp Arg Gly Gly His Val Val Glu Gly
1               5                   10                  15

Leu Ala Gly Glu Leu Gly Gln Leu Arg Ala Arg Leu Glu His His Pro
            20                  25                  30

Gln Gly Gln Arg Glu Pro Leu Val Gln Glu Val Glu Asp Val Asp Glu
        35                  40                  45

Gly Leu Val Gln Asp Leu His Gly Val Val Ala Gly Leu Leu Asp Pro
    50                  55                  60

Val Glu Lys Leu Leu Thr Asp Trp Phe Lys Lys Phe Lys Asn Val Ser
65                  70                  75                  80

Lys Asp Cys Lys Met Thr Phe Tyr Leu Glu Met Tyr Asp Trp Ser Gly
                85                  90                  95

Gly Cys His His His
            100

<210> SEQ ID NO 28
<211> LENGTH: 102
<212> TYPE: PRT
<213> ORGANISM: Artificial sequence
<220> FEATURE:
<223> OTHER INFORMATION: SBP sequence (SB20)

<400> SEQUENCE: 28

Met Asn Glu Lys Thr His Cys Lys Leu Asn Phe Lys Val Asn Ile Ala
1               5                   10                  15

Asp Trp Leu Ala Glu Phe His Gly Gly Gln Gly Leu Leu Gly Arg
            20                  25                  30

Arg Asp Gly Val Val Gln Arg Leu Val Asp Gly Val Gln Glu Arg Val
        35                  40                  45

Glu Arg Leu Asp Arg Asp Pro Gly Leu Gly Asp Leu Arg Leu Glu Leu
    50                  55                  60

His His Arg Asp His Arg Leu Arg Leu Gly Gly Glu His Leu Leu Arg
65                  70                  75                  80

Asp His Pro Leu Glu Pro Asp Asp His Leu Val Val Gly Gly Leu Val

-continued

```
                85                  90                  95
Trp Arg Leu Pro Pro Ser
            100

<210> SEQ ID NO 29
<211> LENGTH: 4531
<212> TYPE: DNA
<213> ORGANISM: Artificial sequence
<220> FEATURE:
<223> OTHER INFORMATION: Expression vector comprising nucleic acids
      encoding CBP and SBP affinity tags

<400> SEQUENCE: 29
atgcattagt tattaatagt aatcaattac ggggtcatta gttcatagcc catatatgga      60
gttccgcgtt acataactta cggtaaatgg cccgcctggc tgaccgccca acgacccccg     120
cccattgacg tcaataatga cgtatgttcc catagtaacg ccaatagga ctttccattg      180
acgtcaatgg gtggagtatt tacgtaaac tgcccacttg gcagtacatc aagtgtatca      240
tatgccaagt acgccccta ttgacgtcaa tgacggtaaa tggcccgcct ggcattatgc      300
ccagtacatg accttatggg actttcctac ttggcagtac atctacgtat tagtcatcgc     360
tattaccatg gtgatgcggt tttggcagta catcaatggg cgtggatagc ggtttgactc     420
acggggattt ccaagtctcc accccattga cgtcaatggg agtttgtttt ggcaccaaaa     480
tcaacgggac tttccaaaat gtcgtaacaa ctccgcccca ttgacgcaaa tgggcggtag     540
gcgtgtacgt gggaggtct atataagcag agctggttta gtgaaccgtc agatccgcta      600
gcgattacgc caagctcgaa attaaccctc actaaaggga caaaagctg gagctccacc      660
gcggtggcgg ccgccaccat gaagcgacga tggaaaaaga atttcatagc cgtctcagca     720
gccaaccgct ttaagaaaat ctcatcctcc gggcacttg aagcggtag cggtaccatg       780
gacgagaaga ccaccggctg gcggggcggc cacgtggtgg agggcctggc cggcgagctg     840
gagcagctgc gggccaggct ggagcaccac cctcagggcc agcgggagcc ctccggcggc     900
tgcaagctgg gctgcccggg cggatccccc gggctgcagg aattcgatat caagcttatc     960
gataccgtcg acctcgaggg ggggcccggt accttaatta ttaaggtac caggtaagtg    1020
tacccaattc gccctatagt gagtcgtatt acaattcact cgatcgccct tcccaacagt    1080
tgcgcagcct gaatggcgaa tggagatcca atttttaagt gtataatgtg ttaaactact    1140
gattctaatt gtttgtgtat tttagattca cagtcccaag gctcatttca ggcccctcag    1200
tcctcacagt ctgttcatga tcataatcag ccataccaca tttgtagagg ttttacttgc    1260
tttaaaaaac ctcccacacc tccccctgaa cctgaaacat aaaatgaatg caattgttgt    1320
tgttaacttg tttattgcag cttataatgg ttacaaataa agcaatagca tcacaaattt    1380
cacaaataaa gcattttttt cactgcattc tagttgtggt ttgtccaaac tcatcaatgt    1440
atcttaacgc gtaaattgta agcgttaata ttttgttaaa attcgcgtta atttttgtt     1500
aaatcagctc attttttaac caataggccg aaatcggcaa aatcccttat aaatcaaaag    1560
aatagaccga gatagggttg agtgttgttc cagtttggaa caagagtcca ctattaaaga    1620
acgtggactc caacgtcaaa gggcgaaaaa ccgtctatca gggcgatggc ccactacgtg    1680
aaccatcacc ctaatcaagt ttttggggt cgaggtgccg taaagcacta atcggaacc      1740
ctaaagggag cccccgattt agagcttgac ggggaaagcc ggcgaacgtg gcgagaaagg    1800
aaggaagaa agcgaaagga gcgggcgcta gggcgctggc aagtgtagcg gtcacgctgc    1860
gcgtaaccac cacacccgcc gcgcttaatg cgccgctaca gggcgcgtca ggtggcactt    1920
```

-continued

```
ttcggggaaa tgtgcgcgga acccctattt gtttatttttt ctaaatacat tcaaatatgt    1980
atccgctcat gagacaataa ccctgataaa tgcttcaata atattgaaaa aggaagaatc    2040
ctgaggcgga agaaccagc tgtggaatgt gtgtcagtta gggtgtggaa agtccccagg     2100
ctccccagca ggcagaagta tgcaaagcat gcatctcaat tagtcagcaa ccaggtgtgg    2160
aaagtcccca ggctcccag caggcagaag tatgcaaagc atgcatctca attagtcagc     2220
aaccatagtc ccgcccctaa ctccgcccat cccgcccta actccgccca gttccgccca     2280
ttctccgccc catggctgac taatttttttt tatttatgca gaggccgagg ccgcctcggc   2340
ctctgagcta ttccagaagt agtgaggagg cttttttgga ggcctaggct tttgcaaaga    2400
tcgatcaaga gacaggatga ggatcgtttc gcatgattga acaagatgga ttgcacgcag    2460
gttctccggc cgcttgggtg gagaggctat tcggctatga ctgggcacaa cagacaatcg    2520
gctgctctga tgccgccgtg ttccggctgt cagcgcaggg gcgcccggtt ctttttgtca    2580
agaccgacct gtccggtgcc ctgaatgaac tgcaagacga ggcagcgcgg ctatcgtggc    2640
tggccacgac gggcgttcct tgcgcagctg tgctcgacgt tgtcactgaa gcgggaaggg    2700
actggctgct attgggcgaa gtgccggggc aggatctcct gtcatctcac cttgctcctg    2760
ccgagaaagt atccatcatg gctgatgcaa tgcggcggct gcatacgctt gatccggcta    2820
cctgcccatt cgaccaccaa gcgaaacatc gcatcgagcg agcacgtact cggatggaag    2880
ccggtcttgt cgatcaggat gatctggacg aagaacatca gggctcgcg ccagccgaac     2940
tgttcgccag gctcaaggcg agcatgcccg acggcgagga tctcgtcgtg acccatggcg    3000
atgcctgctt gccgaatatc atggtggaaa atggccgctt ttctggattc atcgactgtg    3060
gccggctggg tgtggcggac cgctatcagg acatagcgtt ggctacccgt gatattgctg    3120
aagaacttgg cggcgaatgg gctgaccgct tcctcgtgct ttacggtatc gccgctcccg    3180
attcgcagcg catcgccttc tatcgccttc ttgacgagtt cttctgagcg ggactctggg    3240
gttcgaaatg accgaccaag cgacgcccaa cctgccatca cgagatttcg attccaccgc    3300
cgccttctat gaaaggttgg gcttcggaat cgttttccgg gacgccggct ggatgatcct    3360
ccagcgcggg gatctcatgc tggagttctt cgcccaccct aggggaggc taactgaaac     3420
acggaaggag acaataccgg aaggaacccg cgctatgacg gcaataaaaa gacagaataa    3480
aacgcacggt gttgggtcgt ttgttcataa acgcggggtt cggtcccagg ctggcactc     3540
tgtcgatacc ccaccgagac cccattgggg ccaatacgcc cgcgtttctt ccttttcccc    3600
accccacccc caagttcgg gtgaaggccc agggctcgca gccaacgtcg ggcggcagg     3660
ccctgccata gcctcaggtt actcatatat actttagatt gatttaaaac ttcattttta    3720
atttaaaagg atctaggtga agatcctttt tgataatctc atgaccaaaa tcccttaacg    3780
tgagttttcg ttccactgag cgtcagaccc cgtagaaaag atcaaggat cttcttgaga     3840
tcctttttttt ctgcgcgtaa tctgctgctt gcaaacaaaa aaaccaccgc taccagcggt    3900
ggtttgtttg ccggatcaag agctaccaac tcttttttccg aagtaactg gcttcagcag    3960
agcgcagata ccaaatactg tccttctagt gtagccgtag ttaggccacc acttcaagaa    4020
ctctgtagca ccgcctacat acctcgctct gctaatcctg ttaccagtgg ctgctgccag    4080
tggcgataag tcgtgtctta ccgggttgga ctcaagacga tagttaccgg ataaggcgca    4140
gcggtcgggc tgaacggggg gttcgtgcac acagcccagc ttggagcgaa cgacctacac    4200
cgaactgaga tacctacagc gtgagctatg agaaagcgcc acgcttcccg aagggagaaa    4260
```

```
ggcggacagg tatccggtaa gcggcagggt cggaacagga gagcgcacga gggagcttcc    4320 aggggggaaac gcctggtatc tttatagtcc tgtcgggttt cgccacctct gacttgagcg    4380 tcgattttg tgatgctcgt caggggggcg gagcctatgg aaaaacgcca gcaacgcggc     4440 cttttttacgg ttcctggcct tttgctggcc ttttgctcac atgttctttc ctgcgttatc   4500
ccctgattct gtggataacc gtattaccgc c                                   4531
```

<210> SEQ ID NO 30
<211> LENGTH: 4533
<212> TYPE: DNA
<213> ORGANISM: Artificial sequence
<220> FEATURE:
<223> OTHER INFORMATION: Expression vector comprising nucleic acids encoding CBP and SBP affinity tags

<400> SEQUENCE: 30

```
atgcattagt tattaatagt aatcaattac gggtcatta gttcatagcc catatatgga     60
gttccgcgtt acataactta cggtaaatgg cccgcctggc tgaccgccca cgaccccg     120 cccattgacg tcaataatga cgtatgttcc catagtaacg ccaatagggga ctttccattg    180 acgtcaatgg gtggagtatt tacggtaaac tgcccacttg gcagtacatc aagtgtatca    240
tatgccaagt acgccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gcgattacgc caagctcgaa attaaccctc actaaaggga acaaaagctg gagctccacc    660
gcggtggcgg ccgctctagc ccgggcggat ccccgggct gcaggaattc gatatcaagc    720
ttatcgatac cgtcgacact cgagggaagc ggtagcggta ccatggacga aagaccacc    780 ggctggcggg gcgccacgt ggtggagggc ctggccggcg agctgagca gctgcgggcc    840 aggctggagc accaccctca gggccagcgg gagccctccg gcggctgcaa gctgggctcc    900
ggaaagcgac gatggaaaaa gaatttcata gccgtctcag cagccaaccg ctttaagaaa    960
atctcatcct ccgggggcact ttagggcccg gtaccttaat taattaaggt accaggtaag    1020
tgtacccaat tcgccctata gtgagtcgta ttacaattca ctcgatcgcc cttcccaaca    1080
gttgcgcagc ctgaatggcg aatggagatc caatttttaa gtgtataatg tgttaaacta    1140
ctgattctaa ttgtttgtgt attttagatt cacagtccca aggctcattt caggcccctc    1200
agtcctcaca gtctgttcat gatcataatc agccatacca catttgtaga ggttttactt    1260
gctttaaaaa acctcccaca cctcccctg aacctgaaac ataaaatgaa tgcaattgtt    1320
gttgttaact tgtttattgc agcttataat ggttacaaat aaagcaatag catcacaaat    1380
ttcacaaata aagcatttttt ttcactgcat tctagttgtg gtttgtccaa actcatcaat    1440
gtatcttaac gcgtaaattg taagcgttaa tattttgtta aaattcgcgt taaattttg    1500 ttaaatcagc tcatttttta accaataggc cgaaatcggc aaaatccctt ataaatcaaa    1560
agaatagacc gagatagggt tgagtgttgt tccagtttgg aacaagagtc cactattaaa    1620
gaacgtggac tccaacgtca aagggcgaaa aaccgtctat cagggcgatg gcccactacg    1680
tgaaccatca ccctaatcaa gttttttggg gtcgaggtgc cgtaaagcac taaatcggaa    1740
```

```
ccctaaaggg agcccccgat ttagagcttg acggggaaag ccggcgaacg tggcgagaaa    1800
ggaagggaag aaagcgaaag gagcgggcgc tagggcgctg gcaagtgtag cggtcacgct    1860
gcgcgtaacc accacacccg ccgcgcttaa tcgccgcta cagggcgcgt caggtggcac     1920
ttttcgggga aatgtgcgcg gaaccctat ttgtttattt ttctaaatac attcaaatat     1980
gtatccgctc atgagacaat aaccctgata aatgcttcaa taatattgaa aaaggaagaa    2040
tcctgaggcg gaaagaacca gctgtggaat gtgtgtcagt tagggtgtgg aaagtcccca    2100
ggctccccag caggcagaag tatgcaaagc atgcatctca attagtcagc aaccaggtgt    2160
ggaaagtccc caggctcccc agcaggcaga agtatgcaaa gcatgcatct caattagtca    2220
gcaaccatag tcccgcccct aactccgccc atcccgcccc taactccgcc cagttccgcc    2280
cattctccgc cccatggctg actaatttt tttatttatg cagaggccga ggccgcctcg     2340
gcctctgagc tattccagaa gtagtgagga ggcttttttg gaggcctagg cttttgcaaa    2400
gatcgatcaa gagacaggat gaggatcgtt tcgcatgatt gaacaagatg gattgcacgc    2460
aggttctccg gccgcttggg tggagaggct attcggctat gactgggcac aacagacaat    2520
cggctgctct gatgccgccg tgttccggct gtcagcgcag gggcgcccgg ttcttttgt     2580
caagaccgac ctgtccggtg ccctgaatga actgcaagac gaggcagcgc ggctatcgtg    2640
gctggccacg acgggcgttc cttgcgcagc tgtgctcgac gttgtcactg aagcgggaag    2700
ggactggctg ctattgggcg aagtgccggg gcaggatctc ctgtcatctc accttgctcc    2760
tgccgagaaa gtatccatca tggctgatgc aatgcggcgg ctgcatacgc ttgatccggc    2820
tacctgccca ttcgaccacc aagcgaaaca tcgcatcgag cgagcacgta ctcggatgga    2880
agccggtctt gtcgatcagg atgatctgga cgaagaacat caggggctcg cgccagccga    2940
actgttcgcc aggctcaagg cgagcatgcc cgacggcgag gatctcgtcg tgacccatgg    3000
cgatgcctgc ttgccgaata tcatggtgga aaatggccgc ttttctggat tcatcgactg    3060
tggccggctg ggtgtggcgg accgctatca ggacatagcg ttggctaccc gtgatattgc    3120
tgaagaactt ggcggcgaat gggctgaccg cttcctcgtg ctttacggta tcgccgctcc    3180
cgattcgcag cgcatcgcct tctatcgcct tcttgacgag ttcttctgag cgggactctg    3240
gggttcgaaa tgaccgacca agcgacgccc aacctgccat cacgagattt cgattccacc    3300
gccgccttct atgaaaggtt gggcttcgga atcgttttcc gggacgccgg ctggatgatc    3360
ctccagcgcg ggatctcat gctggagttc ttcgcccacc ctaggggag gctaactgaa     3420
acacggaagg agacaatacc ggaaggaacc ccgcgctatga cggcaataaa aagacagaat    3480
aaaacgcacg gtgttgggtc gtttgttcat aaacgcgggg ttcggtccca gggctggcac    3540
tctgtcgata ccccaccgag accccattgg ggccaatacg cccgcgtttc ttcctttcc     3600
ccaccccacc ccccaagttc gggtgaaggc ccagggctcg cagccaacgt cggggcggca    3660
ggccctgcca tagcctcagg ttactcatat atactttaga ttgatttaaa acttcattt     3720
taatttaaaa ggatctaggt gaagatcctt tttgataatc tcatgaccaa aatcccttaa    3780
cgtgagtttt cgttccactg agcgtcagac cccgtagaaa agatcaaagg atcttcttga    3840
gatccttttt ttctgcgcgt aatctgctgc ttgcaaacaa aaaaaccacc gctaccagcg    3900
gtggtttgtt tgccggatca agagctacca actcttttc cgaaggtaac tggcttcagc     3960
agagcgcaga taccaaatac tgtccttcta gtgtagccgt agttaggcca ccacttcaag    4020
aactctgtag caccgcctac atacctcgct ctgctaatcc tgttaccagt ggctgctgcc    4080
agtggcgata agtcgtgtct taccggggttg gactcaagac gatagttacc ggataaggcg    4140
```

-continued

| | |
|---|---|
| cagcggtcgg gctgaacggg gggttcgtgc acacagccca gcttggagcg aacgacctac | 4200 |
| accgaactga gatacctaca gcgtgagcta tgagaaagcg ccacgcttcc cgaagggaga | 4260 |
| aaggcggaca ggtatccggt aagcggcagg gtcggaacag gagagcgcac gagggagctt | 4320 |
| ccaggqggaa acgcctggta tctttatagt cctgtcgggt ttcgccacct ctgacttgag | 4380 |
| cgtcgatttt tgtgatgctc gtcagggggg cggagcctat ggaaaaacgc cagcaacgcg | 4440 |
| gccttttac ggttcctggc cttttgctgg ccttttgctc acatgttctt tcctgcgtta | 4500 |
| tcccctgatt ctgtggataa ccgtattacc gcc | 4533 |

<210> SEQ ID NO 31
<211> LENGTH: 4324
<212> TYPE: DNA
<213> ORGANISM: Artificial sequence
<220> FEATURE:
<223> OTHER INFORMATION: Expression vector for expression of a "target" binding partner

<400> SEQUENCE: 31

| | |
|---|---|
| atgcattagt tattaatagt aatcaattac ggggtcatta gttcatagcc catatatgga | 60 |
| gttccgcgtt acataactta cggtaaatgg cccgcctggc tgaccgccca acgacccccg | 120 |
| cccattgacg tcaataatga cgtatgttcc catagtaacg ccaatagggaa ctttccattg | 180 |
| acgtcaatgg gtggagtatt tacggtaaac tgcccacttg gcagtacatc aagtgtatca | 240 |
| tatgccaagt acgcccccta ttgacgtcaa tgacggtaaa tggcccgcct ggcattatgc | 300 |
| ccagtacatg accttatggg actttcctac ttggcagtac atctacgtat tagtcatcgc | 360 |
| tattaccatg gtgatgcggt tttggcagta catcaatggg cgtggatagc ggtttgactc | 420 |
| acggggattt ccaagtctcc accccattga cgtcaatggg agtttgtttt ggcaccaaaa | 480 |
| tcaacgggac tttccaaaat gtcgtaacaa ctccgcccca ttgacgcaaa tgggcggtag | 540 |
| gcgtgtacgg tgggaggtct atataagcag agctggttta gtgaaccgtc agatccgcta | 600 |
| gcgattacgc caagctcgaa attaaccctc actaaaggga acaaaagctg gagctccacc | 660 |
| gcggtggcgg ccgccaccat ggattacaag gatgacgacg ataagagccc gggcggatcc | 720 |
| cccgggctgc aggaattcga tatcaagctt atcgataccg tcgacctcga ggggggggccc | 780 |
| ggtaccttaa ttaattaagg taccaggtaa gtgtacccaa ttcgccctat agtgagtcgt | 840 |
| attacaattc actcgatcgc ccttcccaac agttgcgcag cctgaatggc gaatggagat | 900 |
| ccaattttta gtgtataat gtgttaaact actgattcta attgtttgtg tattttagat | 960 |
| tcacagtccc aaggctcatt tcaggcccct cagtcctcac agtctgttca tgatcataat | 1020 |
| cagccatacc acatttgtag aggttttact tgctttaaaa aacctcccac acctcccct | 1080 |
| gaacctgaaa cataaaatga atgcaattgt tgttgttaac ttgtttattg cagcttataa | 1140 |
| tggttacaaa taaagcaata gcatcacaaa tttcacaaat aaagcatttt ttcactgca | 1200 |
| ttctagttgt ggtttgtcca aactcatcaa tgtatcttaa cgcgtaaatt gtaagcgtta | 1260 |
| atattttgtt aaaattcgcg ttaaattttt gttaaatcag ctcattttt aaccaatagg | 1320 |
| ccgaaatcgg caaaatccct tataaatcaa aagaatagac cgagataggg ttgagtgttg | 1380 |
| ttccagtttg gaacaagagt ccactattaa agaacgtgga ctccaacgtc aaagggcgaa | 1440 |
| aaaccgtcta tcagggcgat ggcccactac gtgaaccatc accctaatca agttttttgg | 1500 |
| ggtcgaggtg ccgtaaagca ctaaatcgga accctaaagg gagcccccga tttagagctt | 1560 |
| gacggggaaa gccggcgaac gtggcgagaa aggaagggaa gaaagcgaaa ggagcgggcg | 1620 |

```
ctagggcgct ggcaagtgta gcggtcacgc tgcgcgtaac caccacaccc gccgcgctta    1680
atgcgccgct acagggcgcg tcaggtggca cttttcgggg aaatgtgcgc ggaacccccta   1740 tttgtttatt tttctaaata cattcaaata tgtatccgct catgagacaa taaccctgat    1800
aaatgcttca ataatattga aaaggaaga atcctgaggc ggaaagaacc agctgtggaa     1860
tgtgtgtcag ttagggtgtg gaaagtcccc aggctcccca gcaggcagaa gtatgcaaag    1920
catgcatctc aattagtcag caaccaggtg tggaaagtcc ccaggctccc cagcaggcag    1980
aagtatgcaa agcatgcatc tcaattagtc agcaaccata gtcccgcccc taactccgcc    2040
catcccgccc ctaactccgc ccagttccgc ccattctccg ccccatggct gactaatttt    2100
ttttatttat gcagaggccg aggccgcctc ggcctctgag ctattccaga agtagtgagg    2160 aggcttttt ggaggcctag gcttttgcaa agatcgatca agagacagga tgaggatcgt    2220
ttcgcatgat tgaacaagat ggattgcacg caggttctcc ggccgcttgg gtggagaggc    2280
tattcggcta tgactgggca acagacaa tcggctgctc tgatgccgcc gtgttccggc     2340
tgtcagcgca gggcgcccg gttcttttg tcaagaccga cctgtccggt gccctgaatg      2400
aactgcaaga cgaggcagcg cggctatcgt ggctggccac gacgggcgtt ccttgcgcag    2460
ctgtgctcga cgttgtcact gaagcgggaa gggactggct gctattgggc gaagtgccgg    2520
ggcaggatct cctgtcatct caccttgctc ctgccgagaa agtatccatc atggctgatg    2580
caatgcggcg gctgcatacg cttgatccgg ctacctgccc attcgaccac caagcgaaac    2640
atcgcatcga gcgagcacgt actcggatgg aagccggtct tgtcgatcag gatgatctgg    2700
acgaagaaca tcaggggctc gcgccagccg aactgttcgc caggctcaag gcgagcatgc    2760
ccgacggcga ggatctcgtc gtgacccatg gcgatgcctg cttgccgaat atcatggtgg    2820
aaaatggccg cttttctgga ttcatcgact gtggccggct gggtgtggcg gaccgctatc    2880
aggacatagc gttggctacc cgtgatattg ctgaagaact tggcggcgaa tgggctgacc    2940
gcttcctcgt gctttacggt atcgccgctc ccgattcgca gcgcatcgcc ttctatcgcc    3000
ttcttgacga gttcttctga gcgggactct ggggttcgaa atgaccgacc aagcgacgcc    3060
caacctgcca tcacgagatt tcgattccac cgccgccttc tatgaaaggt tgggcttcgg    3120
aatcgttttc cgggacgccg gctggatgat cctccagcgc ggggatctca tgctggagtt    3180
cttcgcccac cctagggga ggctaactga acacggaag gagacaatac cggaaggaac     3240
ccgcgctatg acggcaataa aaagacagaa taaaacgcac ggtgttgggt cgtttgttca    3300
taaacgcggg gttcggtccc agggctggca ctctgtcgat accccaccga gaccccattg    3360
gggccaatac gcccgcgttt cttccttttc cccacccac ccccaagtt cgggtgaagg      3420 cccagggctc gcagccaacg tcgggcggc aggccctgcc atagcctcag gttactcata    3480
tatactttag attgatttaa aacttcattt ttaatttaaa aggatctagg tgaagatcct    3540
ttttgataat ctcatgacca aaatccctta acgtgagttt tcgttccact gagcgtcaga    3600
ccccgtagaa aagatcaaag gatcttcttg agatcctttt tttctgcgcg taatctgctg    3660
cttgcaaaca aaaaaaccac cgctaccagc ggtggtttgt ttgccggatc aagagctacc    3720
aactcttttt ccgaaggtaa ctggcttcag cagagcgcag ataccaaata ctgtccttct    3780
agtgtagccg tagttaggcc accacttcaa gaactctgta gcaccgccta catacctcgc    3840
tctgctaatc ctgttaccag tggctgctgc cagtggcgat aagtcgtgtc ttaccgggtt    3900
ggactcaaga cgatagttac cggataaggc gcagcggtcg ggctgaacgg ggggttcgtg    3960
```

| | |
|---|---|
| cacacagccc agcttggagc gaacgaccta caccgaactg agatacctac agcgtgagct | 4020 |
| atgagaaagc gccacgcttc ccgaagggag aaaggcggac aggtatccgg taagcggcag | 4080 |
| ggtcggaaca ggagagcgca cgagggagct tccaggggga aacgcctggt atctttatag | 4140 |
| tcctgtcggg tttcgccacc tctgacttga gcgtcgattt ttgtgatgct cgtcaggggg | 4200 |
| gcggagccta tggaaaaacg ccagcaacgc ggcctttta cggttcctgg ccttttgctg | 4260 |
| gcctttgct cacatgttct ttcctgcgtt atccctgat tctgtggata accgtattac | 4320 |
| cgcc | 4324 |

<210> SEQ ID NO 32
<211> LENGTH: 4320
<212> TYPE: DNA
<213> ORGANISM: Artificial sequence
<220> FEATURE:
<223> OTHER INFORMATION: Expression vector for expression of a "target" binding partner

<400> SEQUENCE: 32

| | |
|---|---|
| atgcattagt tattaatagt aatcaattac ggggtcatta gttcatagcc catatatgga | 60 |
| gttccgcgtt acataactta cggtaaatgg cccgcctggc tgaccgccca acgaccccg | 120 |
| cccattgacg tcaataatga cgtatgttcc catagtaacg ccaatagga ctttccattg | 180 |
| acgtcaatgg gtggagtatt tacggtaaac tgcccacttg gcagtacatc aagtgtatca | 240 |
| tatgccaagt acgccccta ttgacgtcaa tgacggtaaa tggcccgcct ggcattatgc | 300 |
| ccagtacatg accttatggg actttcctac ttggcagtac atctacgtat tagtcatcgc | 360 |
| tattaccatg gtgatgcggt tttggcagta catcaatggg cgtggatagc ggtttgactc | 420 |
| acggggattt ccaagtctcc accccattga cgtcaatggg agtttgtttt ggcaccaaaa | 480 |
| tcaacgggac tttccaaaat gtcgtaacaa ctccgcccca ttgacgcaaa tgggcggtag | 540 |
| gcgtgtacgt gggaggtct atataagcag agctggttta gtgaaccgtc agatccgcta | 600 |
| gcgattacgc caagctcgaa attaaccctc actaaaggga acaaaagctg gagctccacc | 660 |
| gcggtggcgg ccgctctagc ccgggcggat ccccgggct gcaggaattc gatatcaagc | 720 |
| ttatcgatac cgtcgacact cgaggattac aaggatgacg acgataagta gggcccggta | 780 |
| ccttaattaa ttaaggtacc aggtaagtgt acccaattcg ccctatagtg agtcgtatta | 840 |
| caattcactc gatcgccctt cccaacagtt gcgcagcctg aatggcgaat ggagatccaa | 900 |
| ttttaagtg tataatgtgt taaactactg attctaattg tttgtgtatt ttagattcac | 960 |
| agtcccaagg ctcatttcag gcccctcagt cctcacagtc tgttcatgat cataatcagc | 1020 |
| cataccacat ttgtagaggt tttacttgct taaaaaacc tcccacacct ccccctgaac | 1080 |
| ctgaaacata aaatgaatgc aattgttgtt gttaacttgt ttattgcagc ttataatggt | 1140 |
| tacaaataaa gcaatagcat cacaaatttc acaaataaag catttttttc actgcattct | 1200 |
| agttgtggtt tgtccaaact catcaatgta tcttaacgcg taaattgtaa gcgttaatat | 1260 |
| tttgttaaaa ttcgcgttaa attttgtta aatcagctca tttttaacc ataggccga | 1320 |
| aatcggcaaa atcccttata atcaaaaga atagaccgag ataggttga gtgttgttcc | 1380 |
| agtttggaac aagagtccac tattaaagaa cgtggactcc aacgtcaaag ggcgaaaaac | 1440 |
| cgtctatcag ggcgatggcc cactacgtga accatcaccc taatcaagtt tttggggtc | 1500 |
| gaggtgccgt aaagcactaa atcggaaccc taaagggagc cccgatttag agcttgacg | 1560 |
| gggaaagccg gcgaacgtgg cgagaaagga agggaagaaa gcgaaaggag cgggcgctag | 1620 |

-continued

```
ggcgctggca agtgtagcgg tcacgctgcg cgtaaccacc acacccgccg cgcttaatgc    1680
gccgctacag ggcgcgtcag gtggcacttt tcggggaaat gtgcgcggaa ccccctatttg   1740
tttattttc taaatacatt caaatatgta tccgctcatg agacaataac cctgataaat     1800
gcttcaataa tattgaaaaa ggaagaatcc tgaggcggaa agaaccagct gtggaatgtg    1860
tgtcagttag ggtgtggaaa gtccccaggc tccccagcag gcagaagtat gcaaagcatg    1920
catctcaatt agtcagcaac caggtgtgga aagtccccag gctccccagc aggcagaagt    1980
atgcaaagca tgcatctcaa ttagtcagca accatagtcc cgcccctaac tccgcccatc    2040
ccgcccctaa ctccgcccag ttccgcccat tctccgcccc atggctgact aattttttt    2100
atttatgcag aggccgaggc cgcctcggcc tctgagctat tccagaagta gtgaggaggc    2160
ttttttggag gcctaggctt ttgcaaagat cgatcaagag acaggatgag gatcgtttcg    2220
catgattgaa caagatggat tgcacgcagg ttctccggcc gcttgggtgg agaggctatt    2280
cggctatgac tgggcacaac agacaatcgg ctgctctgat gccgccgtgt tccgctgtc     2340
agcgcagggg cgcccggttc ttttttgtcaa gaccgacctg tccggtgccc tgaatgaact   2400
gcaagacgag gcagcgcggc tatcgtggct ggccacgacg ggcgttcctt gcgcagctgt    2460
gctcgacgtt gtcactgaag cgggaaggga ctggctgcta ttgggcgaag tgccggggca    2520
ggatctcctg tcatctcacc ttgctcctgc cgagaaagta tccatcatgg ctgatgcaat    2580
gcggcggctg catacgcttg atccggctac ctgcccattc gaccaccaag cgaaacatcg    2640
catcgagcga gcacgtactc ggatggaagc cggtcttgtc gatcaggatg atctggacga    2700
agaacatcag gggctcgcgc cagccgaact gttcgccagg ctcaaggcga gcatgcccga    2760
cggcgaggat ctcgtcgtga cccatggcga tgcctgcttg ccgaatatca tggtggaaaa    2820
tggccgcttt tctggattca tcgactgtgg ccggctgggt gtggcggacc gctatcagga    2880
catagcgttg gctacccgtg atattgctga agaacttggc ggcgaatggg ctgaccgctt    2940
cctcgtgctt tacggtatcg ccgctcccga ttcgcagcgc atcgccttct atcgccttct    3000
tgacgagttc ttctgagcgg gactctgggg ttcgaaatga ccgaccaagc gacgcccaac    3060
ctgccatcac gagatttcga ttccaccgcc gccttctatg aaaggttggg cttcggaatc    3120
gttttccggg acgccggctg gatgatcctc cagcgcgggg atctcatgct ggagttcttc    3180
gcccacccta gggggaggct aactgaaaca cggaaggaga caataccgga aggaacccgc    3240
gctatgacgg caataaaaag acagaataaa acgcacggtg ttgggtcgtt tgttcataaa    3300
cgcggggttc ggtcccaggg ctggcactct gtcgataccc caccgagacc ccattggggc    3360
caatacgccc gcgtttcttc cttttcccca ccccaccccc aagttcgggt gaaggccca    3420
gggctcgcag ccaacgtcgg gcggcaggc cctgccatag cctcaggtta ctcatatata    3480
ctttagattg atttaaaact tcatttttaa tttaaaagga tctaggtgaa gatccttttt   3540
gataatctca tgaccaaaat cccttaacgt gagttttcgt tccactgagc gtcagacccc    3600
gtagaaaaga tcaaaggatc ttcttgagat cctttttttc tgcgcgtaat ctgctgcttg    3660
caaacaaaaa aaccaccgct accagcggtg gtttgtttgc cggatcaaga gctaccaact    3720
ctttttccga aggtaactgg cttcagcaga gcgcagatac caaatactgt ccttctagtg    3780
tagccgtagt taggccacca cttcaagaac tctgtagcac cgcctacata cctcgctctg    3840
ctaatcctgt taccagtggc tgctgccagt ggcgataagt cgtgtcttac cgggttggac    3900
tcaagacgat agttaccgga taaggcgcag cggtcgggct gaacggggg ttcgtgcaca    3960
cagcccagct tggagcgaac gacctacacc gaactgagat acctacagcg tgagctatga    4020
```

```
gaaagcgcca cgcttcccga agggagaaag gcggacaggt atccggtaag cggcagggtc    4080
ggaacaggag agcgcacgag ggagcttcca gggggaaacg cctggtatct ttatagtcct    4140
gtcgggtttc gccacctctg acttgagcgt cgattttttgt gatgctcgtc aggggggcgg    4200
agcctatgga aaaacgccag caacgcggcc tttttacggt tcctggcctt ttgctggcct    4260
tttgctcaca tgttctttcc tgcgttatcc cctgattctg tggataaccg tattaccgcc    4320
```